US011529393B2

(12) United States Patent
Lin et al.

(10) Patent No.: US 11,529,393 B2
(45) Date of Patent: Dec. 20, 2022

(54) MESENCHYMAL STEM CELLS EXPRESSING ANTI-INFLAMMATORY CYTOKINES AND METHODS OF USE

(71) Applicant: The Board of Trustees of the Leland Stanford Junior University, Stanford, CA (US)

(72) Inventors: Tzuhua Lin, Stanford, CA (US); Jukka Pajarinen, Stanford, CA (US); Stuart B. Goodman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 605 days.

(21) Appl. No.: 16/340,319

(22) PCT Filed: Oct. 6, 2017

(86) PCT No.: PCT/US2017/055502
§ 371 (c)(1),
(2) Date: Apr. 8, 2019

(87) PCT Pub. No.: WO2018/071295
PCT Pub. Date: Apr. 19, 2018

(65) Prior Publication Data
US 2019/0255151 A1    Aug. 22, 2019

Related U.S. Application Data

(60) Provisional application No. 62/406,342, filed on Oct. 10, 2016.

(51) Int. Cl.
*A01N 63/00*     (2020.01)
*A61K 38/20*     (2006.01)
*A61P 21/00*     (2006.01)
*A61P 19/02*     (2006.01)
*A61P 3/10*      (2006.01)
*A61P 29/00*     (2006.01)
*A61P 19/10*     (2006.01)
*A61K 9/00*      (2006.01)
*A61K 35/28*     (2015.01)
(Continued)

(52) U.S. Cl.
CPC ........ *A61K 38/2026* (2013.01); *A61K 9/0019* (2013.01); *A61K 35/28* (2013.01); *A61K 38/18* (2013.01); *A61K 38/1825* (2013.01); *A61K 38/1841* (2013.01); *A61K 38/1866* (2013.01); *A61K 38/195* (2013.01); *A61K 38/20* (2013.01); *A61K 38/204* (2013.01); *A61K 38/2066* (2013.01); *A61K 38/2073* (2013.01); *A61K 38/2086* (2013.01); *A61P 3/10* (2018.01); *A61P 19/02* (2018.01); *A61P 19/10* (2018.01); *A61P 21/00* (2018.01); *A61P 29/00* (2018.01); *C07K 14/4705* (2013.01); *C07K 14/5406* (2013.01); *C12N 5/0663* (2013.01); *C12N 5/0693* (2013.01); *C12N 15/86* (2013.01); *A61K 2035/124* (2013.01); *C12N 2501/2304* (2013.01); *C12N 2501/60* (2013.01); *C12N 2510/00* (2013.01); *C12N 2529/10* (2013.01); *C12N 2740/15043* (2013.01); *C12Q 1/6897* (2013.01)

(58) Field of Classification Search
None
See application file for complete search history.

(56) References Cited

U.S. PATENT DOCUMENTS

| 2008/0254008 A1 | 10/2008 | Dropulic et al. |
| 2010/0255572 A1 | 10/2010 | Schmidt et al. |
| 2013/0058903 A1 | 3/2013 | Lee |

FOREIGN PATENT DOCUMENTS

| WO | WO 2007127882 | 11/2007 |
| WO | WO 2013114199 | 8/2013 |

(Continued)

OTHER PUBLICATIONS

Uccelli A, Moretta L, Pistoia V. Mesenchymal stem cells in health and disease. Nat Rev Immunol. Sep. 2008;8(9):726-36. (Year: 2008).*
May RD, Fung M. Strategies targeting the IL-4/IL-13 axes in disease. Cytokine. Sep. 2015;75(1):89-116. (Year: 2015).*
Luzina IG, Keegan AD, Heller NM, Rook GA, Shea-Donohue T, Atamas SP. Regulation of inflammation by interleukin-4: a review of "alternatives". J Leukoc Biol. Oct. 2012;92(4):753-64. (Year: 2012).*

(Continued)

*Primary Examiner* — Michael C Wilson
(74) *Attorney, Agent, or Firm* — Kyle A. Gurley; Bozicevic, Field & Francis LLP

(57) ABSTRACT

Provided are compositions and methods for production of anti-inflammatory cytokines, growth factors, or chemokines. Provided are nucleic acids (e.g., expression vectors) that include an NFκB inflammation response element operably linked to a nucleotide sequence encoding an anti-inflammatory cytokine (e.g., IL-4). In some cases, the nucleic acid is an expression vector selected from: a linear expression vector, a circular expression vector, a plasmid, and a viral expression vector. Also provided are cells (e.g., mesenchymal stem cells—MSCs) comprising a nucleic acid that includes an NFκB inflammation response element operably linked to a nucleotide sequence encoding an anti-inflammatory cytokine. In some cases, the nucleic acid is integrated into the cell's genome. Also provided are methods for treating an individual having an inflammation-associated ailment, which can include administering an MSC to the individual, where the MSC includes an NFκB inflammation response element operably linked to a nucleotide sequence encoding an anti-inflammatory cytokine.

15 Claims, 19 Drawing Sheets
Specification includes a Sequence Listing.

(51) Int. Cl.
A61K 38/18 (2006.01)
A61K 38/19 (2006.01)
C12N 15/86 (2006.01)
C12N 5/0775 (2010.01)
C12N 5/09 (2010.01)
C07K 14/54 (2006.01)
C07K 14/47 (2006.01)
A61K 35/12 (2015.01)
C12Q 1/6897 (2018.01)

(56) References Cited

FOREIGN PATENT DOCUMENTS

WO WO 2016026854 2/2016
WO WO 2016081924 5/2016

OTHER PUBLICATIONS

Ankrum JA, Ong JF, Karp JM. Mesenchymal stem cells: immune evasive, not immune privileged. Nat Biotechnol. Mar. 2014;32(3):252-60. (Year: 2014).*
Kean TJ, Lin P, Caplan AI, Dennis JE. MSCs: Delivery Routes and Engraftment, Cell-Targeting Strategies, and Immune Modulation. Stem Cells Int. 2013;2013:732742. (Year: 2013).*
Gibon, et al. "MC3T3-E1 Osteoprogenitor Cells Systemically Migrate to a Bone Defect and Enhance Bone Healing"; Tissue Engineering: Part A; vol. 18, Nos. 9 & 10; 2012; pp. 968-973.
Gibon, et al. "Effect of a CCR1 receptor antagonist on systemic trafficking of MSCs and polyethylene particle-associated bone loss"; Biomaterials; May 2012; 33(14): pp. 3632-3638.
Zwingenberger, et al. "Stem cell attraction via SDF-1α expressing fat tissue grafts"; J Biomed Mater Res A.; Jul. 2013; 101(7): 2067-2074.
Yao, et al. "Mutant monocyte chemoattractant protein 1 protein attenuates migration of and inflammatory cytokine release by macrophages exposed to orthopedic implant wear particles"; J Biomed Mater Res A.; Sep. 2014; 102(9): 3291-3297.
Tuan, et al. "Adult mesenchymal stem cells and cell-based tissue engineering"; Arthritis Res Ther; 2003; 5:32-45.
Arutyunyan, et al. "Umbilical Cord as Prospective Source for Mesenchymal Stem Cell-Based Therapy"; Stem Cells International; vol. 2016; Article ID 6901286; 17 pages.
Payne, et al. "Early intervention with gene-modified mesenchymal stem cells overexpressing interleukin-4 enhances anti-inflammatory responses and functional recovery in experimental autoimmune demyelination"; Cell Adhesion & Migration; May/Jun. 2012; 6:3; 179-189.
Tan, et al. "Exogenous IL-4-Expressing Bone Marrow Mesenchymal Stem Cells for the Treatment of Autoimmune Sensorineural Hearing Loss in a Guinea Pig Model"; BioMed Research International; vol. 2014; Article ID 856019; 10 pages.
Choi, et al. "Mesenchymal stem cells overexpressing interleukin-10 attenuate collagen-induced arthritis in mice"; Clinical and Experimental Immunology; Apr. 7, 2008; 153: 269-276.
Gabner, et al. "Inflammation-induced transgene expression in genetically engineered equine mesenchymal stem cells"; J Gene Med.; Aug. 2016; 18(8): 26 pgs.
Badr, et al. "Real-time monitoring of NF-kappaB activity in cultured cells and in animal models"; Mol Imaging; 2009; 8(5): pp. 1-19.
Carlsen, et al. "In Vivo Imaging of NF-κB Activity"; J Immunol; 2002; 168:1441-1446.
Magness, et al. "In Vivo Pattern of Lipopolysaccharide and Anti-CD3-Induced NF-κB Activation Using a Novel Gene-Targeted Enhanced GFP Reporter Gene Mouse"; J Immunol; 2004; 173:1561-1570.
Lin, et al., "Establishment of NF-κB sensing and IL-4 secreting mesenchymal stromal cells as an "on-demand" drug delivery system to modulate inflammation", Cytotheraphy, (2017); 19(9): 1025-1034.
Mizushima, et al., "pEF-BOS, a powerful mammalian expression vector", Nucleic Acids Research, (1990); vol. 18, No. 17, 5322.
Salmon, et al., "High-level transgene expression in human hematopoietic progenitors and differentiated blood lineages after transduction with improved lentiviral vectors", Gene Therapy, Blood, (2000); vol. 92, No. 10, pp. 3392-3398.
Qin, et al., "Systematic Comparison of Constitutive Promoters and the Doxycycline-Inducible Promoter", PLoS One, (2010), vol. 5, Issue 5, e10611, pp. 1-4.

* cited by examiner

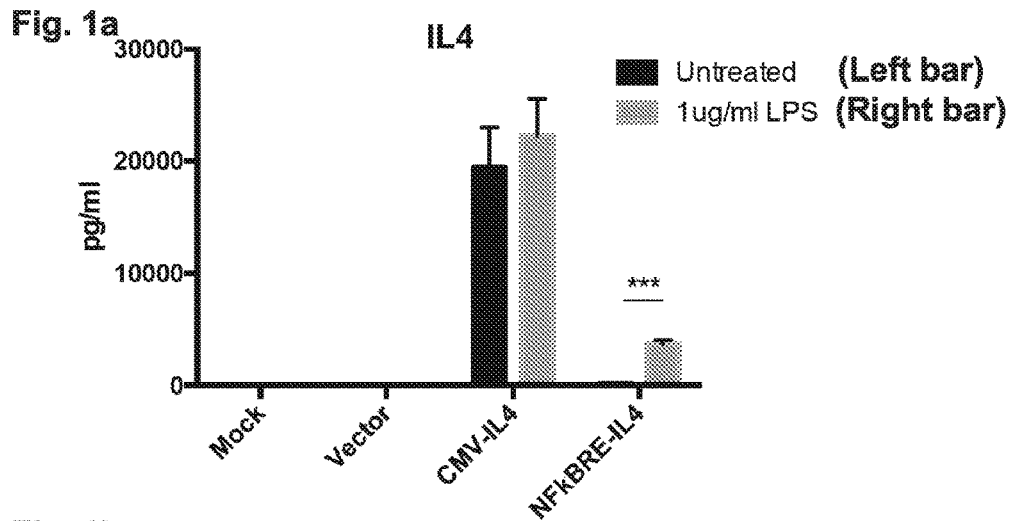
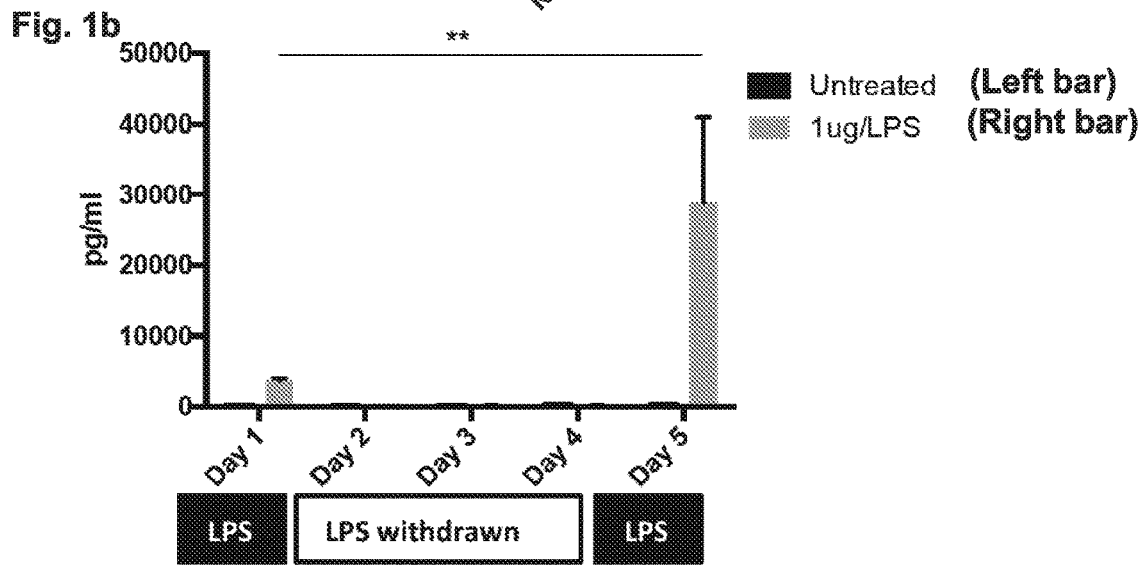
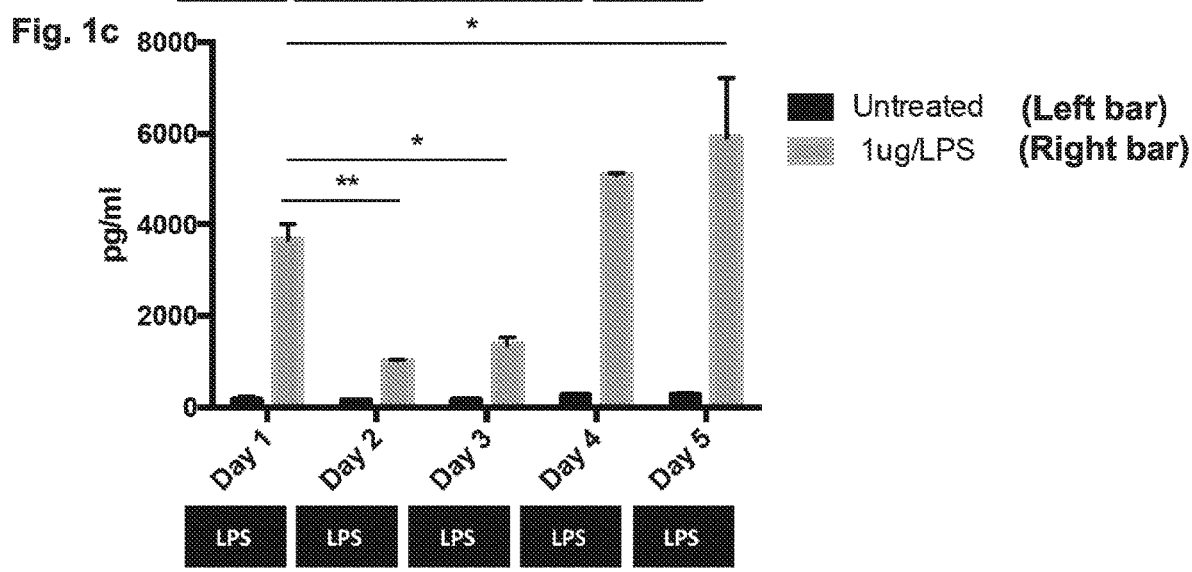

Fig. 8
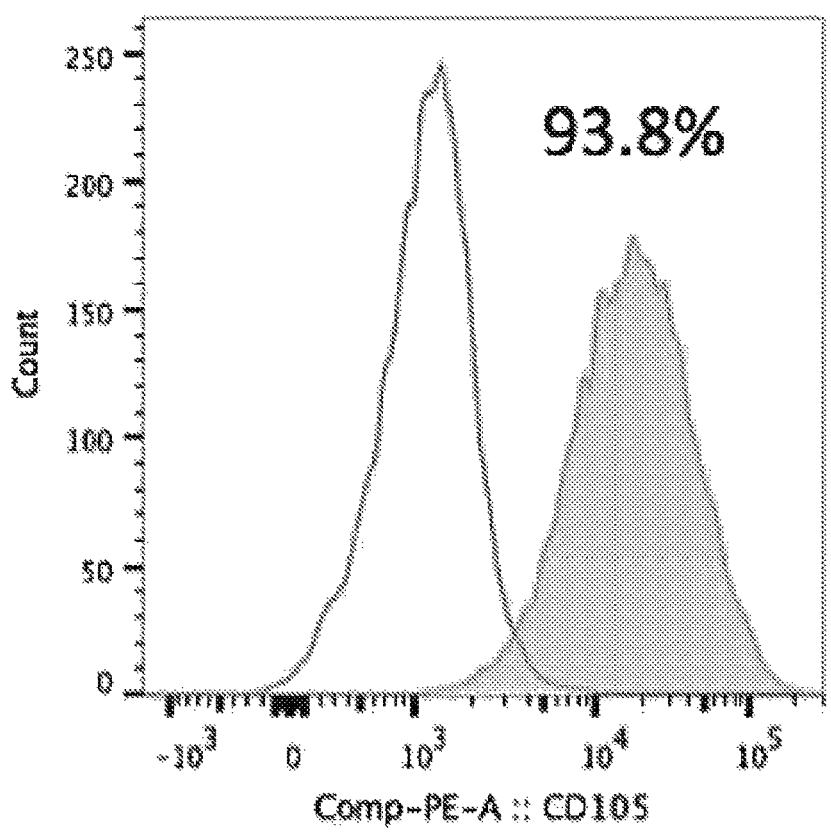
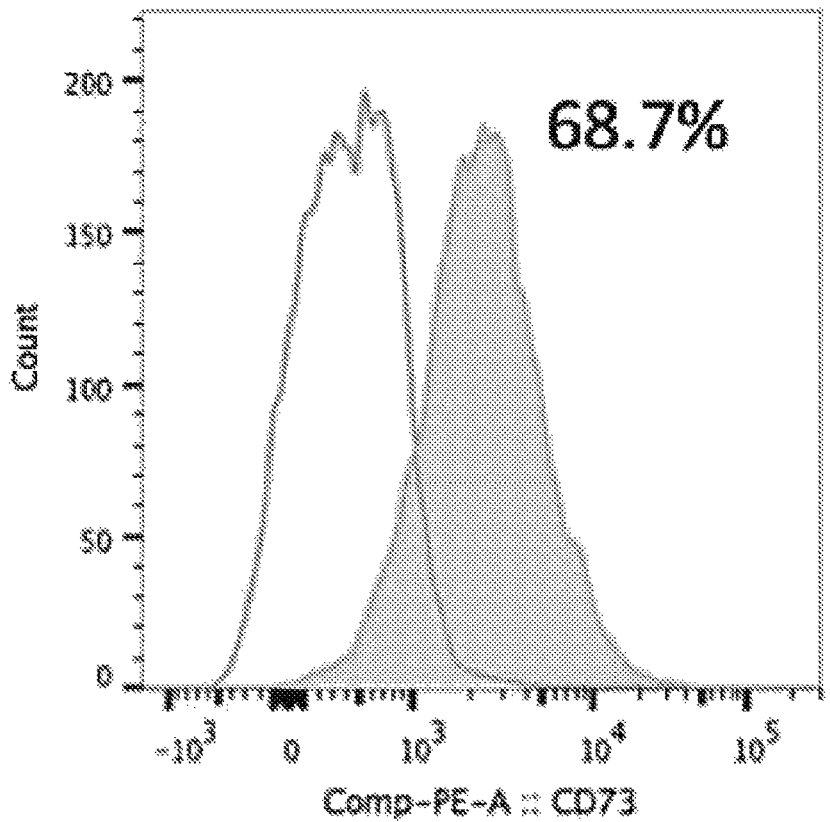

Fig. 8 (Cont. 1)
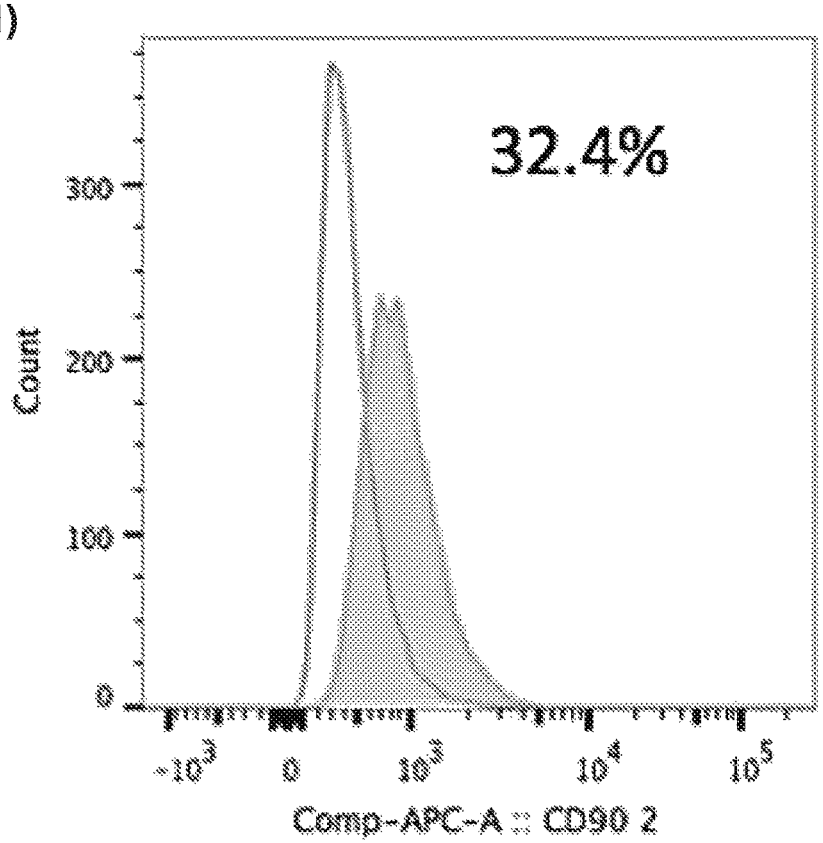
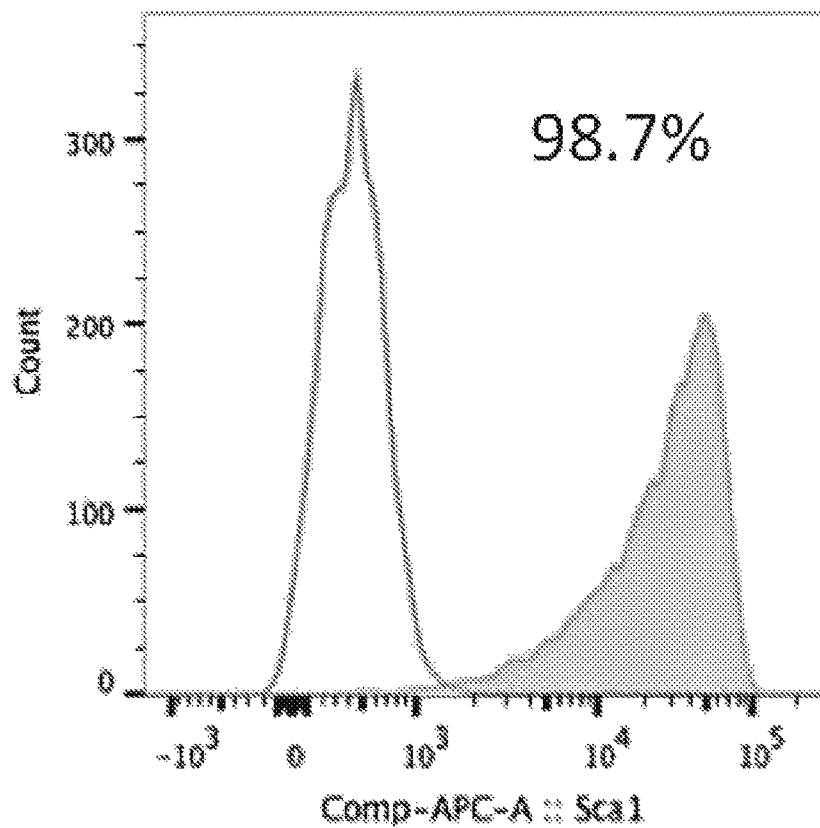

Fig. 8 (Cont. 2)
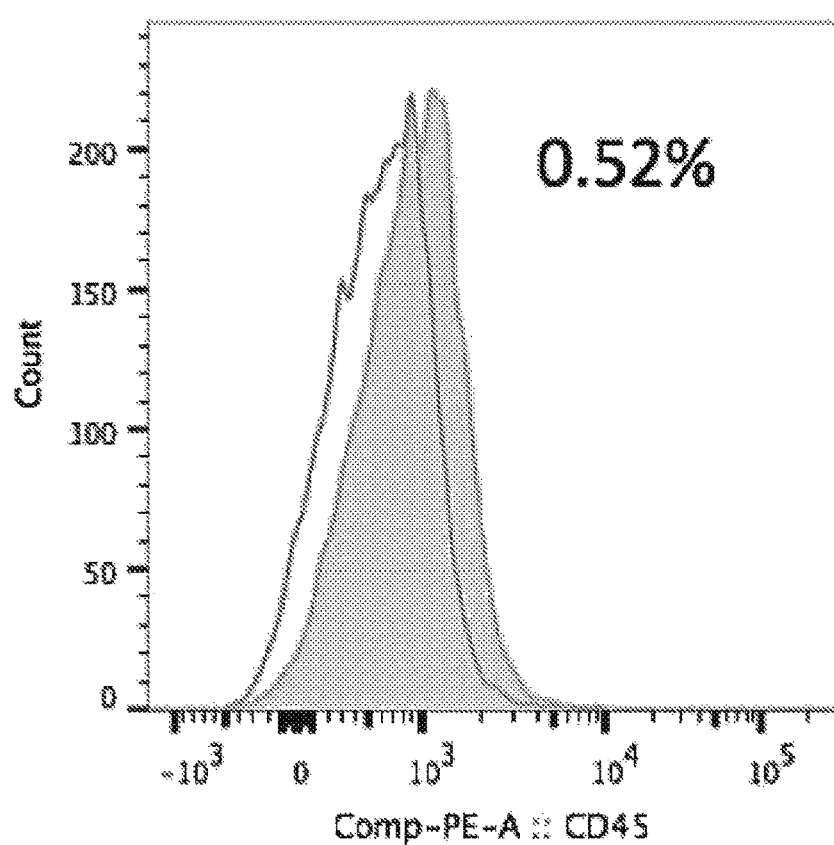
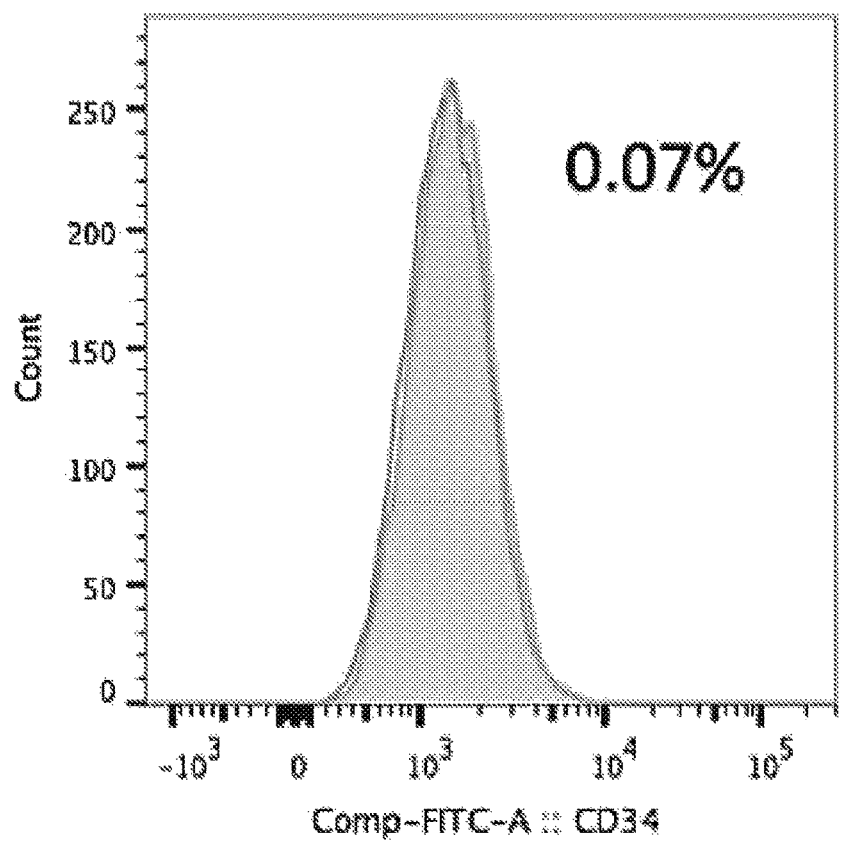

Fig. 8 (Cont. 3)
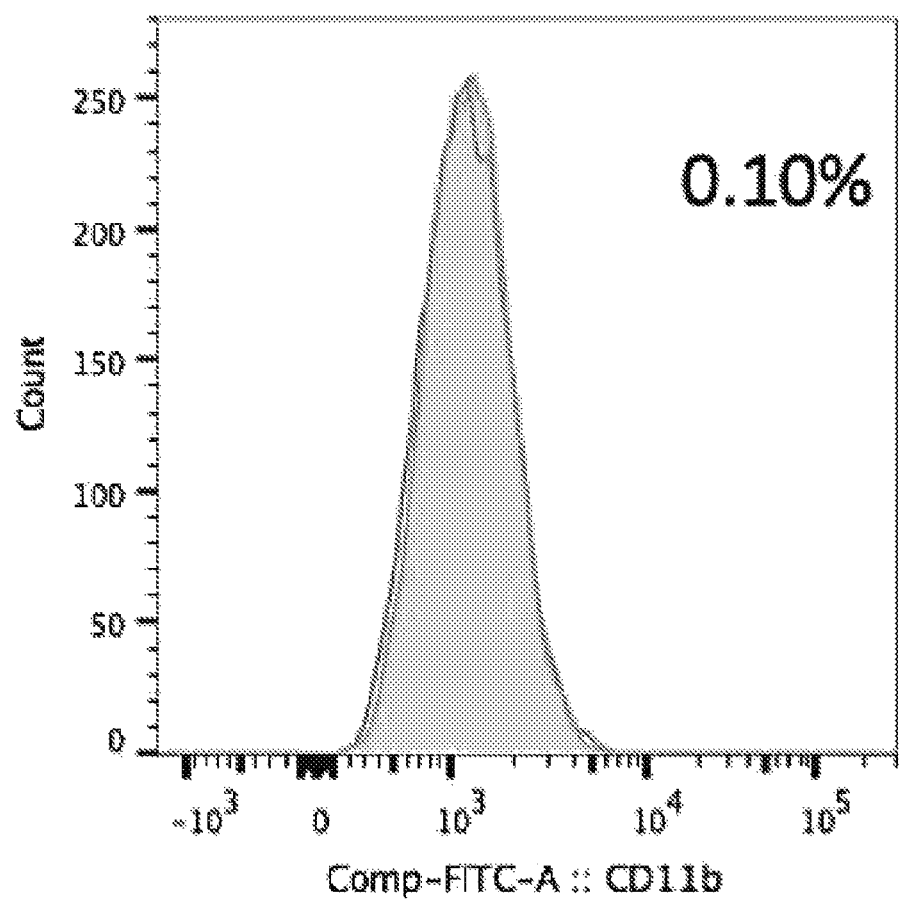

MESENCHYMAL STEM CELLS EXPRESSING ANTI-INFLAMMATORY CYTOKINES AND METHODS OF USE

CROSS-REFERENCE

This application is a national stage entry of International Application No. PCT/US17/55502, filed Oct. 6, 2017, which claims the benefit of U.S. Provisional Patent Application No. 62/406,342, filed Oct. 10, 2016, which application is incorporated herein by reference in its entirety.

INTRODUCTION

Chronic inflammation is associated with secondary symptoms and disorders such as osteolytic bone disorder (bone loss) via excessive inflammatory cytokine secretion by macrophages. Anti-inflammatory cytokines such as IL-4 can convert the macrophage polarization status from an inflammatory type (M1) into anti-inflammatory type (M2).

There is a need for methods and compositions for sensing inflammatory environments and secreting physiological levels of anti-inflammatory cytokines in response.

Publications

Payne et al, Cell Adh Migr. 2012 May-June; 6(3):179-89; Tan et al, Biomed Res Int. 2014; 2014:856019; Choi et al, Clin Exp Immunol. 2008 August; 153(2):269-76; Gabner et al, J Gene Med. 2016 Jun. 6; Badr et al, Mol Imaging. 2009 September-October; 8(5):278-90; Carlsen et al, J Immunol. 2002 Feb. 1; 168(3):1441-6; Magness et al, J Immunol. 2004 Aug. 1; 173(3):1561-70; and patent application Nos. WO2013114199; WO2007127882.

SUMMARY

Provided are compositions for inducible production of anti-inflammatory cytokines (or chemokines or growth factors). Provided are nucleic acids (e.g., expression vectors) that include an NFκB inflammation response element operably linked to a nucleotide sequence encoding an anti-inflammatory cytokine (e.g., IL-4, IL-6, IL-10, IL-11, IL-13, and the like). In some cases, the anti-inflammatory cytokine is IL-4. Also provided are nucleic acids that include an NFκB inflammation response element operably linked to a nucleotide sequence encoding a chemokine, e.g., MCP-1 (CCL2) or SDF-1 (CXCL12). Also provided are nucleic acids that include an NFκB inflammation response element operably linked to a nucleotide sequence encoding a growth factor, e.g, transforming growth factor beta (TGF-beta) vascular endothelial growth factor (VEGF), or fibroblast growth factor (FGF). In some cases, a subject nucleic acid is an expression vector selected from: a linear expression vector, a circular expression vector, a plasmid, and a viral expression vector. In some cases, the expression vector is a lentiviral vector. Also provided are cells (e.g., mesenchymal stem cells—MSCs) comprising a nucleic acid that includes an NFκB inflammation response element operably linked to a nucleotide sequence encoding an anti-inflammatory cytokine (e.g., IL-4, IL-6, IL-10, IL-11, IL-13, and the like) (or encoding a chemokine or growth factor). In some cases, the nucleic acid is integrated into the cell's genome. In some embodiments, a subject cell is an MSC comprising a heterologous nucleic acid comprising an NFκB inflammation response element operably linked to a nucleotide sequence encoding an anti-inflammatory cytokine (e.g., IL-4, IL-6, IL-10, IL-11, and IL-13) (or encoding a chemokine or growth factor). In some cases, the anti-inflammatory cytokine is selected from: IL-4, IL-6, IL-11, and IL-13. In some cases, the anti-inflammatory cytokine is IL-4.

Also provided are methods for treating an individual in need (e.g., an individual having an inflammation-associated ailment, an individual in need of enhanced tissue regeneration such as an individual healing from a fracture, and the like). Such methods can include a step of administering a mesenchymal stem cell (MSC) (e.g., a population of MSCs) to the individual, where the MSC comprises a heterologous nucleic acid comprising an NFκB inflammation response element operably linked to a nucleotide sequence encoding an anti-inflammatory cytokine (e.g., IL-4, IL-6, IL-10, IL-11, IL-13, and the like) (or encoding a chemokine such as MCP-1 or SDF-1, or encoding a growth factor such as TGF-beta, VEGF, or FGF). In some cases, the anti-inflammatory cytokine is selected from: IL-4, IL-6, IL-11, and IL-13. In some cases, the anti-inflammatory cytokine is IL-4. In some cases, the individual has chronic inflammation. In some cases, the individual has one or more of: a bone injury, osteoarthritis, rheumatoid arthritis, a cardiovascular disease, hepatic inflammation, a myocardial infarction, musculoskeletal inflammation, neurological associated inflammation, diabetes, and a spinal cord injury. In some cases, the individual has an inflammation associated ailment. In some cases, the individual is recovering from an injury and would benefit from enhanced tissue regeneration (e.g., fracture healing).

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1a-1c provides data related to the secretion profile of NFκB sensing and IL-4 secreting MSCs in response to lipopolysaccharide (LPS).

(FIG. 6a) Illustration of IL-4 secreting MSC-mediated immunomodulation on macrophage polarization. The conditioned media collected from untreated MSCs (vector and NFκBRE-IL4) was used to treat for 24 hours with freshly added LPS (1 µg/ml). M1 (FIG. 6b-6e) and M2 (FIG. 6f-6i) macrophage markers were analyzed by quantitative PCR (FIG. 6b, 6c, 6f, 6g, 6h) or ELISA (FIG. 6d, 6e, 6i). The ratio of TNFα and IL-1RA production was determined to highlight balance of pro- and anti-inflammatory factors (FIG. 6e) The difference between LPS treated groups was analyzed by one-way ANOVA. *p<0.05, p<0.01, *p<0.005

FIG. 8. Immunophenotypes characterization of murine bone marrow-derived MSC. The MSC surface marker expression (CD105+/CD73+/CD90.2+/Sca1+CD45−/CD34−CD11b−) was examined by flow cytometry.

(FIG. 9a) Illustration of $MSC^V$ conditioned media affect macrophage polarization. The conditioned media collected from $MSC^V$ exposed to 1 µg/ml LPS or LPS alone were used to treat macrophages for 24 hours. M1 (FIG. 9b-9c), IL-10 (FIG. 9d), and M2 (FIG. 9e-9g) macrophage markers were analyzed by quantitative PCR. The difference between LPS treated groups was analyzed by one-way ANOVA. *p<0.05, p<0.01, *p<0.005.

DETAILED DESCRIPTION

Figure 2A:
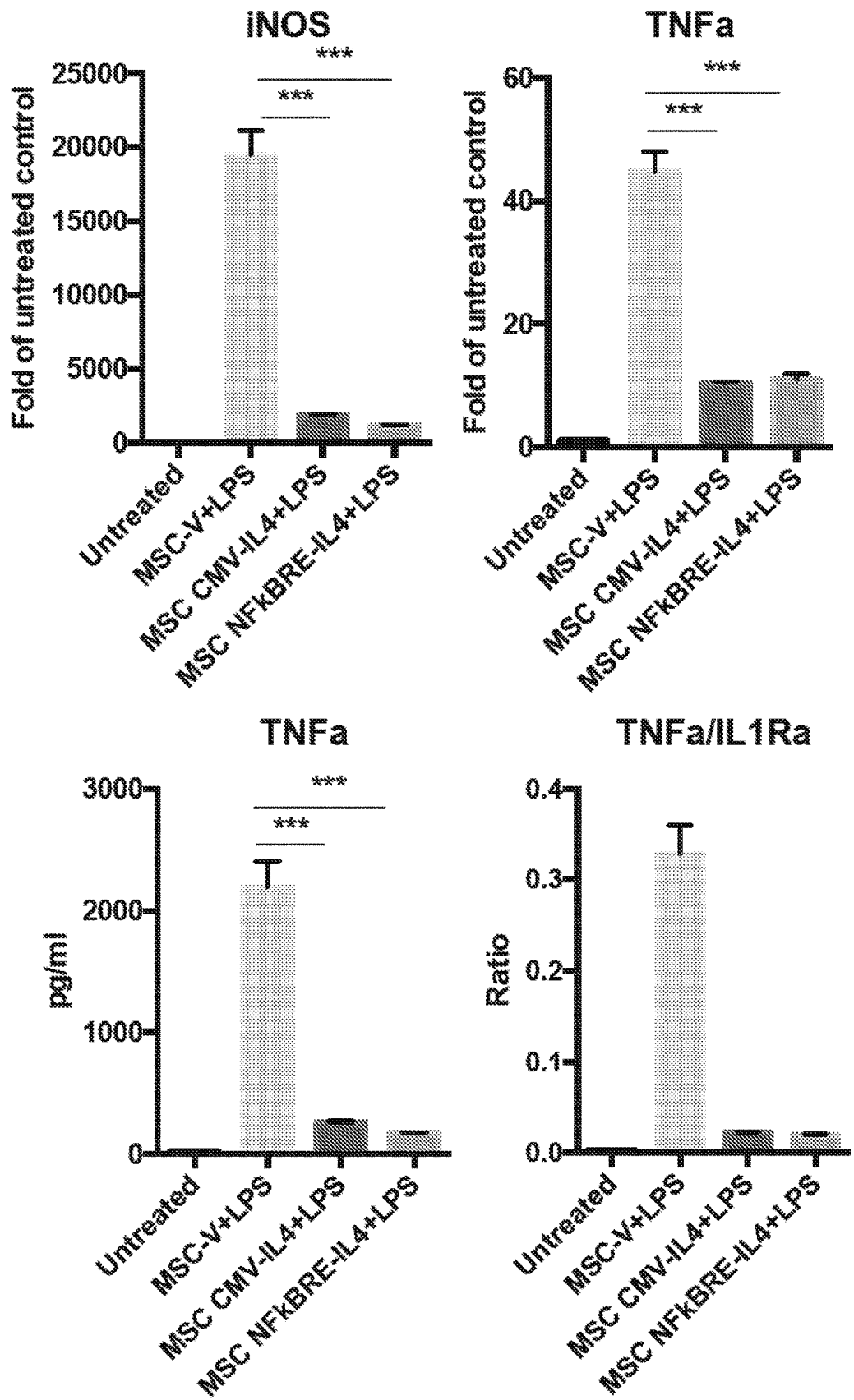
FIG. 2a-2b provides data related to the modulation of macrophage polarization by NFκB sensing IL-4 secreting MSCs in response to LPS.

Provided are compositions for inducible production of anti-inflammatory cytokines.

Provided are nucleic acids (e.g., expression vectors) that include an NFκB inflammation response element operably linked to a nucleotide sequence encoding an anti-inflammatory cytokine (e.g., IL-4, IL-6, IL-10, IL-11, IL-13, and the like). In some cases, the anti-inflammatory cytokine is IL-4. In some cases, the nucleic acid is an expression vector selected from: a linear expression vector, a circular expression vector, a plasmid, and a viral expression vector. In some cases, the expression vector is a lentiviral vector. Also provided are cells (e.g., mesenchymal stem cells—MSCs) comprising a nucleic acid that includes an NFκBinflammation response element operably linked to a nucleotide sequence encoding an anti-inflammatory cytokine (e.g., IL-4, IL-6, IL-10, IL-11, IL-13, and the like). In some cases, the nucleic acid is integrated into the cell's genome. In some embodiments, a subject cell is an MSC comprising a heterologous nucleic acid comprising an NFκB inflammation response element operably linked to a nucleotide sequence encoding an anti-inflammatory cytokine (e.g., IL-4, IL-6, IL-11, and IL-13). In some cases, the anti-inflammatory cytokine is IL-4.

Also provided are methods for treating an individual in need (e.g., an individual having an inflammation-associated ailment). Such methods can include a step of administering a mesenchymal stem cell (MSC) (e.g., a population of MSCs) to the individual, where the MSC comprises a heterologous nucleic acid comprising an NFκB inflammation response element operably linked to a nucleotide sequence encoding an anti-inflammatory cytokine (e.g., IL-4, IL-6, IL-10, IL-11, IL-13, and the like). In some cases, the anti-inflammatory cytokine is IL-4

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Compositions and Methods The inventors have discovered that NFκB-dependent regulation of anti-inflammatory cytokine production (or chemokine production or growth factor production) in mesenchymal stem cells (MSCs) allows the MSCs to sense the inflammatory environment and secret physiological levels of a desired anti-inflammatory cytokine (e.g., IL-4) (or a desired chemokine or growth factor). The secretion will be turn off when the inflammation has been resolved. Also, the secretion can be turned on again in the presence of inflammatory signals. This inflammation-sensing model minimizes the potential side effects from the constitutive and excess amount of target protein secretion using traditional strategy.

Nucleic Acids

Provided are nucleic acids that include an NFκB inflammation response element operably linked to a nucleotide sequence encoding an anti-inflammatory cytokine (e.g., IL-4, IL-6, IL-10, IL-11, and IL-13). In some cases, the anti-inflammatory cytokine is selected from: IL-4, IL-6, IL-10, IL-11, and IL-13. In some cases, the anti-inflammatory cytokine is selected from: IL-4, IL-6, IL-11, and IL-13. In some cases, the anti-inflammatory cytokine is IL-4.

The protein sequence of Homo sapiens IL-4 (interleukin 4) is MGLTSQLLPPLFFLLACAG-NFVHGHKCDITLQEIIKTLNSLTEQKTLCTELTVTDI-FAASKNTT EKETFCRAATVLRQFYSHHEKDTRCL-GATAQQFHRHKQURFLKRLDRNLWGLAGLNSCP VKEANQSTLENFLERLKTIMREKYSKCSS (SEQ ID NO: 16). The protein sequence of Mus musculus (mouse) IL-4 (interleukin 4) is MGLNPQLVVILLFFLECTR-SHIHGCDKNHLREIIGILNEVTGEGTPCTEMDVPNVL-TATKNTT ESELVCRASKVLRIFYLKHGKTPCLK-KNSSVLMELQRLFRAFRCLDSSISCTMNESKSTSLK DFLESLKSIMQMDYS (SEQ ID NO: 11).

The protein sequence of Homo sapiens IL-6 (interleukin 6) is MNSFSTSAFGPVAFSLGLLLVLPAAF-PAPVPPGEDSKDVAAPHRQPLTSSERIDKQIRYILD GISALRKETCNKSNMCESSKEALAENNLNLPK-MAEKDGCFQSGFNEETCLVKIITGLLEFEV YLEY-LQNRFESSEEQARAVQMSTKVLIQFLQKKAKNL-DAITTPDPTTNASLLTKLQAQNQW LQDMTTHLILRSFKEFLQSSLRALRQM (SEQ ID NO: 17). The protein sequence of Mus musculus (mouse) IL-6 (interleukin 6) is MKFLSARDFHPVAFLGLMLVTT-TAFPTSQVRRGDFTEDTTPNRPVYTTSQVG-GLITHVLWE IVEMRKELCNGNSDCMNNDDA-LAENNLKLPEIQRNDGCYQTGYNQEICLLKISSGLLEYHS YLEYMKNNLKDNKKDKARVLQRDTETLI-HIFNQEVKDLHKIVLPTPISNALLTDKLESQKEWL RTKTIQFILKSLEEFLKVTLRSTRQT (SEQ ID NO: 12).

The protein sequence of Homo sapiens IL-10 (interleukin 10) is MHSSALLCCLVLLTGVRASPGQGTQSEN-SCTHFPGNLPNMLRDLRDAFSRVKTFFQMKD QLDNLLLKESLLEDFKGYLGCQALSEMI-QFYLEEVMPQAENQDPDIKAHVNSLGENLKTLR LRLRRCHRFLPCENK-SKAVEQVKNAFNKLQEKGIYKAMSEFDI-FINYIEAYMTMKIRN (SEQ ID NO: 18). The protein sequence of Mus musculus (mouse) IL-10 (interleukin 10) is MPGSALLCCLLLLTGMRIS-RGQYSREDNNCTHFPVGQSHMLLELR-TAFSQVKTFFQTKDQ LDNILLTD-SLMQDFKGYLGCQALSEMIQFYLVEVMPQAEKHGP-EIKEHLNSLGEKLKTLRM RLRRCHRFLPCENK-SKAVEQVKSDFNKLQDQGVYKAMNEFDIFIN-CIEAYMMIKMKS (SEQ ID NO: 13).

The protein sequence of Homo sapiens IL-11 (interleukin 11) is MNCVCRLVLVVLSLWPDTAVAPGPPPGP-PRVSPDPRAELDSTVLLTRSLLADTRQLAAQL RDKF-PADGDHNLDSLPTLAMSAGALGALQLPGVLTRL-RADLLSYLRHVQWLRRAGGSSLK TLEPELGTLQARLDRLLRRLQLLMSRLALPQPPPDP-PAPPLAPPSSAWGGIRAAHAILGGL HLTLDWAVR-GLLLLKTRL (SEQ ID NO: 19). The protein sequence of Mus musculus (mouse) IL-11 (interleukin 11) is MNCVCRLVLVVLSLWPDRWAPGP-PAGSPRVSSDPRADLDSAVLLTRSLLADTRQLAAQM RDKFPADGDHSLDSLPTLAMSAGTLGSLQLPGVL-TRLRVDLMSYLRHVQWLRRAGGPSLK TLEPEL-GALQARLERLLRRLQLLMSRLALPQAAP-DQPVIPLGPPASAWGSIRAAHAILGGLH LTLDWAVRGLLLLKTRL (SEQ ID NO: 14).

The protein sequence of Homo sapiens IL-13 (interleukin 13) is MHPLLNPLLLALGLMALLLTTVIALT-CLGGFASPGPVPPSTALRELIEELVNITQNQKAPLCN GSMVWSINLTAGMYCAALESLINVSGC-SAIEKTQRMLSGFCPHKVSAGQFSSLHVRDTKIE VAQFVKDLLLHLKKLFREGQFN (SEQ ID NO: 20). The protein sequence of Mus musculus (mouse) IL-13 (interleukin 13) is MALMTAVLALACLGG-LAAPGPVPRSVSLPLTLKELIEELSNITQDQTPLCNG-SMVWSVDL AAGGFCVALDSLTNIS-NCNAIYRTQRILHGLCNRKAPTTVSSLPDTKIEVAH-FITKLLSYTKQL FRHGPF (SEQ ID NO: 15).

Also provided are nucleic acids that include an NFκB inflammation response element operably linked to a nucleotide sequence encoding a chemokine. In some cases the chemokine is selected from Table 1. In some cases the chemokine is selected from MCP-1 (CCL2) and SDF-1 (CXCL12). Also provided are nucleic acids that include an NFκB inflammation response element operably linked to a nucleotide sequence encoding a growth factor. In some cases the growth factor is selected from transforming growth factor beta (TGF-beta) (e.g., TGFβ1, TGFβ2, TGFβ3, TGFβ4); vascular endothelial growth factor (VEGF); and fibroblast growth factor (FGF) (e.g., FGF1, FGF2, FGF3, FGF4, FGF5, FGF6, FGF7, FGF8, FGF9, FGF10, FGF16, FGF17, FGF18, FGF19, FGF20, FGF21, FGF22, FGF23, and the like).

TABLE 1

| Chemokines. | |
| --- | --- |
| Common Name | Systemic name |
| Gro alpha | CXCL1 |
| Gro beta | CXCL2 |
| Gro gamma | CXCL3 |
| PF4 | CXCL4 |
| ENA-78 | CXCL5 |
| GCP-2 | CXCL6 |
| NAP-2 | CXCL7 |
| IL-8 | CXCL8 |

TABLE 1-continued

Chemokines.

| Common Name | Systemic name |
|---|---|
| Mig | CXCL9 |
| IP-10 | CXCL10 |
| I-TAC | CXCL11 |
| SDF-1 (alpha/beta) | CXCL12 |
| BCA-1 | CXCL13 |
| BRAK | CXCL14 |
| Lungkine | CXCL15 |
|  | CXCL16 |
| Fractalkine | CX3CL1 |
| I-309 | CCL1 |
| MCP-1 | CCL2 |
| MIP-1 alpha | CCL3 |
| MIP-1 beta | CCL4 |
| RANTES | CCL5 |
| C10 | CCL6 |
| MCP-3 | CCL7 |
| MCP-2 | CCL8 |
| MIP-1 gamma | CCL9/10 |
| Eotaxin | CCL11 |
| MCP-5 | CCL12 |
| MCP-4 | CCL13 |
| HCC-1 | CCL14 |
| HCC-2 | CCL15 |
| HCC-4 | CCL16 |
| TARC | CCL17 |
| PARC | CCL18 |
| ELC | CCL19 |
| MIP-3 alpha | CCL20 |
| SLC | CCL21 |
| MDC | CCL22 |
| MPIF-1 | CCL23 |
| Eotaxin-2 | CCL24 |
| TECK | CCL25 |
| Eotaxin-3 | CCL26 |
| CTACK | CCL27 |
| MEC | CCL28 |
| LD-78 beta | CCL3L1 |
| Lymphotactin | XCL1 |
| SCM-1 beta | XCL2 |

NFκB Inflammation Response Element

In some embodiments (e.g., in some MSCs, in some nucleic acids, in some methods of treatment, and the like), a constitutive promoter (instead of an NFκB inflammation response element) is operably linked to the nucleotide sequence encoding the anti-inflammatory cytokine (or encoding a chemokine such as MCP-1 or SDF-1, or encoding a growth factor such as TGF-beta, VEGF, or FGF). In some embodiments (e.g., in some MSCs, in some nucleic acids, in some methods of treatment, and the like), an inducible promoter (e.g., drug inducible promoter, instead of an NFκB inflammation response element) is operably linked to the nucleotide sequence encoding the anti-inflammatory cytokine (or encoding a chemokine such as MCP-1 or SDF-1, or encoding a growth factor such as TGF-beta, VEGF, or FGF). In some embodiments (e.g., in some MSCs, in some nucleic acids, in some methods of treatment, and the like), a tissue-specific promoter (e.g., in addition to or instead of an NFκB inflammation response element) is operably linked to the nucleotide sequence encoding the anti-inflammatory cytokine (or encoding a chemokine such as MCP-1 or SDF-1, or encoding a growth factor such as TGF-beta, VEGF, or FGF).

In some embodiments, an NFκB inflammation response element is operably linked to the nucleotide sequence encoding the anti-inflammatory cytokine (or encoding a chemokine such as MCP-1 or SDF-1, or encoding a growth factor such as TGF-beta, VEGF, or FGF). In some cases, this is in addition to a promoter (e.g., a mini-promoter as is used in the examples section below). NFκB inflammation response elements are known in the art and any convenient NFκB inflammation response element can be used. An NFκB inflammation response element is a transcriptional control element that can be operably linked to a nucleotide sequence of interest (e.g., one encoding an anti-inflammatory cytokine) such that transcription of the nucleotide sequence of interest is controlled by the NFκB signaling pathway. In this way inflammation, which triggers signaling through the NFκB signaling pathway, triggers expression of the nucleotide sequence of interest.

An NFκB inflammation response element includes one or more binding sites that are bound by NFκB in response to inflammation (i.e., NFκB inflammation binding sites). In cases where a binding site is repeated, and/or more than one binding site is used in an NFκB inflammation response element, the binding sites can be connected in tandem and/or can overlap with one another.

Examples of NFκB inflammation binding sites include but are not limited to: GGGAATTTCC (SEQ ID NO: 3), GGGGACTTTC (SEQ ID NO: 4), GGGACTTTCC (SEQ ID NO: 5), GGGGACTTTCC (SEQ ID NO: 6), and TGGGGACTTTCCGC (SEQ ID NO: 7).

Examples of NFκB inflammation response elements that include a repeated binding site and/or more than one binding site include but are not limited to:

(SEQ ID NO: 1)
GGGAATTTCC<u>GGGGACTTTCC</u>GGGAATTTCC<u>GGGGACTTTC</u>CGGGAATTT

CC
and (SEQ ID NO: 2)
TGGGGACTTTCCGCTGGGGACTTTCCGCTGGGGACTTTCCGCTGGGGACT

TTCCGCTGGGGACTTTCCGC.

In the example set forth as SEQ ID NO: 1, the NFκB inflammation binding site GGGAATTTCC (SEQ ID NO: 3) is present 3 times (bold), the NFκB inflammation binding site GGGGACTTTC (SEQ ID NO: 4) is present 2 times (underline), and the NFκB inflammation binding site GGGACTTTCC (SEQ ID NO: 5) is present 2 times (italics). The binding sites of SEQ ID NOs 4 and 5 overlap. Put another way, the NFκB inflammation binding site (A) [GGGAATTTCC (SEQ ID NO: 3)] is present 3 times and is intercalated with the NFκB inflammation binding site (B) [GGGGACTTTCC (SEQ ID NO: 6)], which is present 2 times, such that the pattern of NFκB inflammation binding sites in the NFκB inflammation response element set forth as SEQ ID NO: 1 is (A)-(B)-(A)-(B)-(A).

In the example set forth as SEQ ID NO: 2, the NFκB inflammation binding site (A) TGGGGACTTTCCGC (SEQ ID NO: 7) is present 5 times in tandom such that the pattern of NFκB inflammation binding sites in the NFκB inflammation response element set forth as SEQ ID NO: 2 is (A)-(A)-(A)-(A)-(A). Because the NFκB inflammation binding sites set forth as SEQ ID NOs: 4 and 6 are each a subset of the sequence set forth as SEQ ID NO: 7, they each are also present 5 times in the example set forth as SEQ ID NO: 2.

In some cases, an NFκB inflammation response element includes the nucleotide sequence set forth in SEQ ID NO: 1. In some cases, an NFκB inflammation response element includes the nucleotide sequence set forth in any one of SEQ ID NOs: 1-2. In some cases, an NFκB inflammation response element includes one or more repeats (e.g., 2 or more, 3 or more, 4 or more, or 5 or more repeats) of a binding site selected from those set forth as SEQ ID NOs: 3-7. In some cases, an NFκB inflammation response element includes from 1-10 binding sites (e.g., from 1-8, 1-5, 2-10, 2-8, 2-5, 3-10, 3-8, 3-5, 4-10, 4-8, 4-5, 5-10, or 5-8 binding sites) selected from those set forth as SEQ ID NOs: 3-7. In some cases, an NFκB inflammation response element includes at least 5 NFκB inflammation binding sites, where each of the 5 sites is independently selected from those set forth as SEQ ID NOs: 3-7.

Vectors

A "vector" is a replicon, such as plasmid, phage, virus, or cosmid, to which another DNA segment, i.e., an "insert" (e.g., a nucleic acid that includes an NFκB inflammation response element operably linked to a nucleotide sequence encoding an anti-inflammatory cytokine such as IL-4, IL-6, IL-10, IL-11, or IL-13; or encoding a chemokine such as MCP-1 or SDF-1, or encoding a growth factor such as TGF-beta, VEGF, or FGF), may be attached so as to bring about the replication of the insert in a cell.

An "expression cassette" comprises a DNA coding sequence (e.g., a nucleotide sequence encoding a polypeptide such as an anti-inflammatory cytokine) operably linked to a transcriptional control element. "Operably linked" refers to a juxtaposition wherein the components so described are in a relationship permitting them to function in their intended manner. For instance, a control element is operably linked to a coding sequence (and likewise the coding sequence is operably linked to the control element) if the control element affects transcription/expression of the coding sequence. As would be readily understood by one of ordinary skill in the art, a nucleotide sequence can be operably linked to more than one control element (e.g., a promoter and a NFκB inflammation response element).

The terms "recombinant expression vector," "expression vector" and similar terms of the art are used interchangeably herein to refer to a DNA molecule comprising a vector and at least one insert, where the insert includes an expression cassette (e.g., an NFκB inflammation response element operably linked to a nucleotide sequence encoding an anti-inflammatory cytokine). Recombinant expression vectors can be generated for the purpose of expressing and/or propagating the insert(s) (e.g., in bacteria), or for the construction of other recombinant nucleotide sequences. In some cases, a subject nucleic acid (e.g., an expression cassette, an expression vector, a viral expression vector, a linear expression vector, a circular expression vector, a plasmid, and the like) includes an NFκB inflammation response element operably linked to a nucleotide sequence encoding an anti-inflammatory cytokine (e.g., IL-4, IL-6, IL-10, IL-11, or IL-13)(or encoding a chemokine such as MCP-1 or SDF-1, or encoding a growth factor such as TGF-beta, VEGF, or FGF).

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (HIV) (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); lentiviral vector (e.g., a CD511B-1 lentiviral expression vector modified to include an NFκB inflammation response element operably linked to a nucleotide sequence encoding an anti-inflammatory cytokine); and the like.

Numerous suitable expression vectors are known to those of skill in the art, and many are commercially available. The following vectors are provided by way of example as vectors that can be modified to include an NFκB inflammation response element operably linked to a nucleotide sequence encoding an anti-inflammatory cytokine (or encoding a chemokine such as MCP-1 or SDF-1, or encoding a growth factor such as TGF-beta, VEGF, or FGF): pXT1, pSG5 (Stratagene), pSVK3, pBPV, pMSG, pCMV3, pGL4.32 [luc2/NF-κB-RE/Hygro], and pSVLSV40 (Pharmacia). However, any convenient vector can be used and many suitable vectors will be known to one of ordinary skill in the art.

Cells (e.g., Genetically Modified Cells)

Provided are cells (genetically modified cells) that include a heterologous nucleic acid (e.g., a nucleic acid, e.g., an expression vector, that includes an NFκB inflammation response element operably linked to a nucleotide sequence encoding an anti-inflammatory cytokine such as IL-4, IL-6, IL-10, IL-11, or IL-13) (or encoding a chemokine such as MCP-1 or SDF-1, or encoding a growth factor such as TGF-beta, VEGF, or FGF). In cases where the heterologous nucleic acid is not integrated into the cell's genome (e.g., is maintained extrachromosomally, 'episomally'), the cell is still referred to herein as genetically modified. In some embodiments, the heterologous nucleic acid is integrated into the cell's genome (e.g., randomly integrated or integrated into a particular site such as a safe harbor site, e.g., see Sadelain et al., Nat Rev Cancer. 2011 Dec. 1; 12(1):51-8).

A cell that includes a subject heterologous nucleic acid (e.g., a nucleic acid that includes an NFκB inflammation response element operably linked to a nucleotide sequence encoding an anti-inflammatory cytokine such as IL-4, IL-6, IL-10, IL-11, or IL-13; or encoding a chemokine such as MCP-1 or SDF-1; or encoding a growth factor such as TGF-beta, VEGF, or FGF) can be any cell. Such a cell can be a cell from any organism (e.g., a bacterial cell, an archaeal cell, a cell of a single-cell eukaryotic organism, a plant cell, an algal cell, a fungal cell (e.g., a yeast cell), an animal cell, a cell from an invertebrate animal (e.g., fruit fly, mosquito, cnidarian, echinoderm, nematode, etc.), a cell from a vertebrate animal (e.g., fish, amphibian, reptile, bird, mammal), a cell from a mammal, a cell from a rodent, a cell from a human, etc.). For example, suitable cells include prokaryotic cells such as bacterial cells (e.g., *E. coli*), e.g., for the purpose of vector propagation. As noted above, suitable cells also include eukaryotic cells such as mammalian cells, rodent cells, mouse cells, rat cells, primate cells, non-human primate cells, and human cells. In some cases (e.g., in some cases where the cell will be used in a method of treatment), the cell is a mesenchymal stem cell (MSC) (e.g., a human MSC).

Mesenchymal Stem Cells (MSCs)

Provided are compositions and methods that include a cell that comprises a nucleic acid as described above (a heterologous nucleic acid, e.g., a nucleic acid that includes an NFκB inflammation response element operably linked to a nucleotide sequence encoding an anti-inflammatory cytokine such as IL-4, IL-6, IL-10, IL-11, or IL-13)(or encoding a chemokine such as MCP-1 or SDF-1, or encoding a growth factor such as TGF-beta, VEGF, or FGF), and in some cases, the cell is a mesenchymal stem cell (MSC). The adult bone marrow has been generally considered to include hematopoietic tissue and the associated supporting stroma. Within the latter compartment, a subset of cells with multipotent differentiation capacity exists, usually referred to as mesenchymal stem cells. Mesenchymal stem cells can easily be expanded ex vivo and induced to differentiate into several cell types, including osteoblasts, adipocytes and chondrocytes. The term "MSC" is used herein interchangeably with the terms 'mesenchymal stem cells', 'marrow stromal cells', 'bone marrow stromal cells', 'BM stromal cells', and 'mesenchymal stromal cells.'

As used herein, e.g., when referring to human MSCs, the term refers to those cells that meet the minimal criteria to define human MSCs as proposed by the Mesenchymal and Tissue Stem Cell Committee of the International Society for Cellular Therapy (ISCT): (1) MSCs are plastic-adherent when maintained in standard culture conditions; (2) MSCs express CD105, CD73, and CD90 and lack expression of CD45, CD34, CD14 or CD11b, CD79a or CD19, and HLA-DR surface molecules; and (3) MSCs differentiate into osteoblasts, adipocytes, and chondroblasts in vitro (e.g., see Dominici et al., Cytotherapy. 2006;8(4):315-7).

It will be understood by those of skill in the art that expression levels reflect detectable amounts of the marker (e.g., nucleic acid or protein) on and/or in the cell. A cell that is negative for staining (e.g., the level of binding of a marker specific reagent is not detectably different from a matched control) may still express minor amounts of the marker. And while it is commonplace in the art to refer to cells as "positive" or "negative" for a particular marker, actual expression levels are quantitative traits. The number of detected molecules can vary by several logs, yet still be characterized as "positive".

When a protein marker is used, the staining intensity (e.g., of a marker-specific antibody) can be monitored by flow cytometry, where lasers detect the quantitative levels of fluorochrome (which is proportional to the amount of cell marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell can be recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining brighter than that of an isotype matched control, but is not as intense as the most brightly staining cells normally found in the population. An alternative control may utilize a substrate having a defined density of marker on its surface, for example a fabricated bead or cell line, which can provide the positive control for intensity.

MSCs can be isolated from a number of sources and cells from any convenient source can be used. In some cases, MSCs are isolated from bone marrow (BM-MSCs). Although bone marrow-derived MSCs are the most extensively characterized, MSCs can be isolated from other sources as well, including but not necessarily limited to: adipose tissue, peripheral blood, umbilical cord blood, amniotic fluid, skin, dental pulp, synovium, umbilical cord tissue, placental complex, tendon, gut, muscle, cartilage, and endometrium. Some evidence suggests that MSCs may be present virtually in any vascularized tissue throughout the whole body (e.g., see Arutyunyan et. al., Stem Cells Int. 2016; 2016:6901286; Prockop, Science. 1997 Apr. 4; 276(5309): 71-4; and Tuan et. al., Arthritis Res Ther. 2003; 5(1):32-45). An MSC isolated from any source, including those listed above, can be used in the compositions and methods of this disclosure.

Various ways to isolate MSCs are known in the art and any convenient method can be used. For example, one protocol for isolating MSCs from mouse compact bone includes flushing bone marrow out of long bones, digesting the bone chips with collagenase type II, deprivation of the released cells, and culturing the digested bone fragments, out of which fibroblast-like cells migrate and grow in the defined medium. MSCs are also commercially available. For additional information related to MSCs and various ways to isolate them, see, e.g., Zhu et. al., "A protocol for isolation and culture of mesenchymal stem cells from mouse compact bone" Nat Protoc. 2010 March; 5(3):550-60; Lin et. al., J Orthop Res. 2016 Apr. 22; Gibon et. al., Stem Cell Res Ther. 2016 Mar. 22; 7:44; Loi et. al., Bone. 2016 May; 86:119-30. doi: 10.1016/j.bone.2016.02.020; Yao et. al., J Biomed Mater Res A. 2014 September; 102(9):3291-7; xx et. al., J Biomed Mater Res A. 2013 July; 101(7):2067-74; Gibon et. al., Biomaterials. 2012 May; 33(14):3632-8; Pittenger et. al., Science. 1999 Apr. 2; 284(5411):143-7; Arutyunyan et. al., Stem Cells Int. 2016; 2016:6901286; Noth et. al., J Orthop Res. 2002 September; 20(5):1060-9; Watson et. al., Stem Cell Res Ther. 2014 Apr. 15; 5(2):51, Lee et. al., Tissue Eng Part C Methods. 2016 Sep. 28; Li et. al., Ann N Y Acad Sci. 2016 April; 1370(1):109-18; and Caterson et. al., Mol Biotechnol. 2002 March; 20(3):245-56; as well as U.S. Pat. Nos. 9,456,893; 9,458,429; 9,457,051; 9,434,925; and 9,421,304, all of which are hereby incorporated by reference in their entirety.

A number of scientific publications have described the underlying biology of MSCs, preclinical studies for the use of MSCs in regenerative medicine in various fields have been performed, and the efficacy of MSCs has been determined in several clinical trials. MSCs for use in the subject methods can be isolated by any convenient method, and many such methods will be known to one of ordinary skill in the art. For example, in some cases MSCs are isolated from bone marrow, expanded in culture (at which time a subject heterologous nucleic acid can in some cases be introduced), and then transplanted into an individual.

Genetically Modified Non-Human Mammals

Provided are genetically modified non-human mammals that include a subject heterologous nucleic acid (that includes an NFκB inflammation response element operably linked to a nucleotide sequence encoding an anti-inflammatory cytokine such as IL-4, IL-6, IL-10, IL-11, or IL-13; or encoding a chemokine such as MCP-1 or SDF-1; or encoding a growth factor such as TGF-beta, VEGF, or FGF)

integrated into its genome. Suitable non-human mammals include but are not limited to: rodents (e.g., mice, rats), ungulates, pigs, sheep, cattle, horses, camels, rabbits, guinea pigs, and non-human primates such as monkeys. In some cases, the genetically modified non-human mammal is a rodent (e.g., a mouse, a rat). In some cases, the genetically modified non-human mammal is a non-human primate (e.g., a monkey).

Methods of Treatment

Aspects of the disclosure include methods of treating an individual (e.g., method of enhancing tissue regeneration, method of reducing inflammation, and the like). The subject methods of treatment can include administering a subject nucleic acid (e.g., an expression vector, a viral vector, etc.) to an individual (e.g., such that the nucleic acid is introduced into MSCs of the individual). The subject methods of treatment can include administering (e.g., injecting, transplanting, etc.) an effective number of MSCs into an individual, where the MSCs include a subject heterologous nucleic acid (e.g., one that includes an NFκB inflammation response element operably linked to a nucleotide sequence encoding an anti-inflammatory cytokine, e.g., IL-4, IL-6, IL-10, IL-11, IL-13; or encoding a chemokine such as MCP-1 or SDF-1; or encoding a growth factor such as TGF-beta, VEGF, or FGF). Thus, a subject method of treatment can be considered to be an immunomodulation therapy (an immunomodulatory treatment). Administration of subject MSCs can be used to stimulate (enhance) tissue regeneration, and thus in some cases a subject method of treatment is a method of enhancing (stimulating) tissue regeneration/repair (e.g., wound healing, fracture healing, bone healing, skin healing, soft tissue healing, and the like). As discussed in more detail above, the MSCs can be from any source and can be derived by any convenient method.

In some cases the MSCs are autologous (i.e., from the same individual into which they will be administered, e.g., after introduction of a subject heterologous nucleic acid). In other words, in some cases, MSCs are isolated from an individual, genetically modified to include a heterologous nucleic acid that includes an NFκB inflammation response element operably linked to a nucleotide sequence encoding an anti-inflammatory cytokine (e.g., IL-4, IL-6, IL-10, IL-11, IL-13) (or encoding a chemokine such as MCP-1 or SDF-1, or encoding a growth factor such as TGF-beta, VEGF, or FGF), and then re-introduced (e.g., in some cases after culturing/proliferating outside of the body) back into the same individual. The heterologous nucleic in some cases integrates into the genome of the MSC(s) and in some cases it remains extrachromosomal. In some cases, the MSCs are from a related individual (e.g., to reduce the possibility and/or severity of an immune response). In some cases, the MSCs are from an unrelated individual. In some cases, the MSCs are from an individual of another species (e.g., human MSCs administered/transplanted to a mouse).

In some cases, MSCs are cultured for a period of time prior to transplantation into an individual. Cells (e.g., MSCs) can be provided to the individual (i.e., administered into the individual) alone or with a suitable substrate or matrix, e.g. to support their growth and/or organization in the tissue to which they are being transplanted. In some embodiments, MSCs are delivered using a scaffold (e.g., a matrix, an organ scaffold, a bioengineered tissue scaffold such as a chitosan/alginate/hydroxyapatite scaffold, a fibrin scaffold, a ceramic scaffold, a porous ceramic scaffold, a micropatterned scaffold, and the like). Any convenient tissue scaffold can be used and numerous tissue scaffolds for cell delivery/implantation will be known to one of ordinary skill in the art.

Examples of tissue scaffolds (e.g., for soft tissue reconstruction, for articular cartilage reconstruction, for bone healing, for cartilage repair, for fracture healing, for wound healing/repair, for skin wound healing, and the like) include but are not limited to those found in U.S. Pat. Nos. 9,456,893, 9,456,890, 9,456,819, 9,446,164, 9,440,007, 9,440,006, 9,439,764, 9,439,642, 9,439,636, 9,433,701, 9,427,496, 9,421,306, 9,421,304, 9,421,082, 9,408,615, 9,402,803, 9,398,948, 9,394,435, 9,393,347, 9,393,344, 9,389,336, 9,387,281, 9,387,280, 9,381,274, and 9,192,655, all of which are herein incorporated by reference in their entirety. For additional examples, see Lin et al., J Biomed Mater Res A. 2016 September; 104(9):2234-42; Wahl et al., Biomed Res Int. 2015;2015; Diniz et. al., J Mater Sci Mater Med. 2015 March; 26(3):153; Wang et al., J Dent Res. 2014 July; 93(7):618-25; Hyatt et al., Neurosci Lett. 2014 May 21; 569:12-7; Diao et al., Regen Med. 2013 May; 8(3):257-69; Lee et al., Acta Biomater. 2011 August; 7(8):3178-86; Guo et al., Biomed Mater. 2006 September; 1(3):93-9; Howard et al., J Anat. 2008 July; 213(1):66-72; Formigli et al., Wound Repair Regen. 2015 January-February; 23(1):115-23; and Sun et al., PLoS One. 2013 Sep. 5; 8(9):e74672; all of which are herein incorporated by reference in their entirety.

In some embodiments, subject cells are administered into the individual on microcarriers (e.g., cells grown on biodegradable microcarriers). The term "microcarrier culture" is used herein to refer to the culture of cells on a support matrix (e.g., a spherical support matrix). In this system, cells are propagated on the surface of small solid particles suspended in the growth medium by slow agitation. The cells attach and grow to confluence on the surface of the microcarriers, and microcarriers can then be implanted/delivered.

In some embodiments, $1 \times 10^3$ or more cells will be administered (e.g., transplanted), for example $5 \times 10^3$ or more cells, $1 \times 10^4$ or more cells, $5 \times 10^4$ or more cells, $1 \times 10^5$ or more cells, $5 \times 10^5$ or more cells, $1 \times 10^6$ or more cells, $5 \times 10^6$ or more cells, $1 \times 10^7$ or more cells, $5 \times 10^7$ or more cells, $1 \times 10^8$ or more cells, $5 \times 10^8$ or more cells, $1 \times 10^9$ or more cells, $5 \times 10^9$ or more cells, or $1 \times 10^{10}$ or more cells.

The cells induced by the subject methods (MSCs) may be administered in any physiologically acceptable excipient (e.g., William's E medium), where the cells may find an appropriate site for survival and function. The cells may be introduced to the subject (i.e., administered into the individual) via any of the following routes: parenteral, subcutaneous, intravenous, intracranial, intraspinal, intraocular, into spinal fluid, and the like. The cells may be introduced by injection (e.g., direct local injection), catheter, or the like. Examples of methods for local delivery include, e.g., bolus injection, e.g. by a syringe, e.g., into a joint or organ; e.g., by continuous infusion, e.g. by cannulation, or by implanting a device upon which the cells have been reversably affixed (see e.g. US Application Nos. 20080081064 and 20090196903, incorporated herein by reference).

The number of administrations of treatment to a subject may vary. Introducing cells into an individual may be a one-time event; but in certain situations, such treatment may elicit improvement for a limited period of time and require an on-going series of repeated treatments. In other situations, multiple administrations of MSCs may be required before an effect is observed. As will be readily understood by one of ordinary skill in the art, the exact protocols depend upon the disease or condition, the stage of the disease and parameters of the individual being treated.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., with an inflammatory disease/ailment) as well as those in which prevention is desired.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including rodents, rats, mice, primates, non-human primates humans, domestic and farm animals, and zoo, sports, or pet animals, such as dogs, horses, cats, cows, sheep, goats, pigs, camels, etc. In some embodiments, the mammal is human.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

In some embodiments, the individual to be treated is an individual with an inflammatory condition (e.g., an inflammatory-associated disease) (e.g., chronic inflammation). For example, the compositions and methods disclosed herein are appropriate for treatment of any clinical scenario in which unwanted inflammation is present in any body system or disease entity. Examples of symptoms, ailments, illnesses, and/or diseases that can be treated (e.g., by transplanting a subject genetically modified MSC or population of MSC(s) into an individual), include, but are not limited to: bone injury (individuals who are undergoing bone healing), osteoarthritis, rheumatoid arthritis, cardiovascular disease, hepatic inflammation, myocardial infarction, musculoskeletal inflammation, neurological associated inflammation, diabetes, and spinal cord injury. Because chronic inflammation can lead to osteolytic bone disorders (bone loss), in some cases a subject individual has an osteolytic bone disorder. In some cases, the individual to be treated has an inflammatory-associated disease selected from: bone injury (individuals who are undergoing bone healing), osteoarthritis, rheumatoid arthritis, cardiovascular disease, hepatic inflammation, myocardial infarction, musculoskeletal inflammation, neurological associated inflammation, diabetes, and spinal cord injury.

Because the anti-inflammatory cytokine (e.g., IL-4) secreted by a subject MSCs can re-program local inflammatory M1 macrophages into M2 phenotype, MSCs that include a heterologous nucleic acid (e.g., one that includes an NFκB inflammation response element operably linked to a nucleotide sequence encoding an anti-inflammatory cytokine, e.g., IL-4, IL-6, IL-10, IL-11, IL-13)(or encoding a chemokine such as MCP-1 or SDF-1, or encoding a growth factor such as TGF-beta, VEGF, or FGF) can also be used for methods of enhancing (stimulating) (e.g., speeding up) tissue regeneration (e.g., fracture healing, wound healing, tissue repair). In other words, in addition to reducing inflammation, MSCs of the disclosure induce (enhance, stimulate) healing. Thus, in some cases, a subject method of treatment is a method of enhancing (stimulating) tissue regeneration. In some cases, a subject method of treatment is a method of enhancing (stimulating) tissue healing. In some cases, a subject method of treatment is a method of enhancing (stimulating) fracture healing.

The term "population", e.g., "cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of MSCs is an amount that is sufficient, when administered to (e.g., transplanted into) the individual, to palliate, ameliorate, stabilize, reverse, prevent, slow or delay the progression of the disease state (e.g., inflammation) by, for example, providing reducing excessive inflammation.

In some embodiments, a therapeutically effective dose of MSCs is about $1 \times 10^3$ or more cells (e.g., $5 \times 10^3$ or more, $1 \times 10^4$ cells, $5 \times 10^4$ or more, $1 \times 10^5$ or more, $5 \times 10^5$ or more, $1 \times 10^8$ or more, $5 \times 10^6$ or more, $1 \times 10^7$ cells, $5 \times 10^7$ or more, $1 \times 10^8$ or more, $5 \times 10^8$ or more, $1 \times 10^9$ or more, $5 \times 10^9$ or more, or $1 \times 10^{10}$ or more). In some embodiments, a therapeutically effective dose of MSCs is in a range of from about $1 \times 10^3$ cells to about $1 \times 10^{10}$ cells (e.g, from about $5 \times 10^3$ cells to about $1 \times 10^{10}$ cells, from about $1 \times 10^4$ cells to about $1 \times 10^{10}$ cells, from about $5 \times 10^4$ cells to about $1 \times 10^{10}$ cells, from about $1 \times 10^5$ cells to about $1 \times 10^{10}$ cells, from about $5 \times 10^5$ cells to about $1 \times 10^{10}$ cells, from about $1 \times 10^6$ cells to about $1 \times 10^{10}$ cells, from about $5 \times 10^6$ cells to about $1 \times 10^{10}$ cells, from about $1 \times 10^7$ cells to about $1 \times 10^{10}$ cells, from about $5 \times 10^7$ cells to about $1 \times 10^{10}$ cells, from about $1 \times 10^8$ cells to about $1 \times 10^{10}$ cells, from about $5 \times 10^8$ cells to about $1 \times 10^{10}$, from about $5 \times 10^3$ cells to about $5 \times 10^9$ cells, from about $1 \times 10^4$ cells to about $5 \times 10^9$ cells, from about $5 \times 10^4$ cells to about $5 \times 10^9$ cells, from about $1 \times 10^5$ cells to about $5 \times 10^9$ cells, from about $5 \times 10^5$ cells to about $5 \times 10^9$ cells, from about $1 \times 10^6$ cells to about $5 \times 10^9$ cells, from about $5 \times 10^6$ cells to about $5 \times 10^9$ cells, from about $1 \times 10^7$ cells to about $5 \times 10^9$ cells, from about $5 \times 10^7$ cells to about $5 \times 10^9$ cells, from about $1 \times 10^8$ cells to about $5 \times 10^9$ cells, from about $5 \times 10^8$ cells to about $5 \times 10^9$, from about $5 \times 10^3$ cells to about $1 \times 10^9$ cells, from about $1 \times 10^4$ cells to about $1 \times 10^9$ cells, from about $5 \times 10^4$ cells to about $1 \times 10^9$ cells, from about $1 \times 10^5$ cells to about $1 \times 10^9$ cells, from about $5 \times 10^5$ cells to about 1×10$^9$ cells, from about 1×10$^6$ cells to about 1×10$^9$ cells, from about 5×10$^6$ cells to about 1×10$^9$ cells, from about 1×10$^7$ cells to about 1×10$^9$ cells, from about 5×10$^7$ cells to about 1×10$^9$ cells, from about 1×10$^8$ cells to about 1×10$^9$ cells, from about 5×10$^8$ cells to about 1×10$^9$, from about 5×10$^3$ cells to about 5×10$^8$ cells, from about 1×10$^4$ cells to about 5×10$^8$ cells, from about 5×10$^4$ cells to about 5×10$^8$ cells, from about 1×10$^5$ cells to about 5×10$^8$ cells, from about 5×10$^5$ cells to about 5×10$^8$ cells, from about 1×10$^6$ cells to about 5×10$^8$ cells, from about 5×10$^6$ cells to about 5×10$^8$ cells, from about 1×10$^7$ cells to about 5×10$^8$ cells, from about 5×10$^7$ cells to about 5×10$^8$ cells, or from about 1×10$^8$ cells to about 5×10$^8$ cells).

The cells of this disclosure can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods may be genetically altered in order to introduce genes useful in the MSCs, e.g. repair of a genetic defect in an individual, selectable marker, etc. Cells may also be genetically modified to enhance survival, control proliferation, and the like. Cells may be genetically altered by transfection or transduction with a suitable vector, homologous recombination, or other appropriate technique, so that they express a gene of interest. In some embodiments, a selectable marker is introduced, to provide for greater purity of the desired cell.

As described above, many vectors useful for transferring exogenous nucleic acids into target mammalian cells (e.g., MSCs) are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. In some cases, lentiviral vectors are used. Lentiviral vectors such as those based on HIV or FIV gag sequences can be used to transfect non-dividing cells, such as the resting phase of human stem cells (see Uchida et al. (1998) PNAS. 95(20):11939-44).

Nucleic Acid Delivery

In some embodiments a subject method is method of nucleic acid delivery (a method of delivering a heterologous nucleic acid (one that includes an NFκB inflammation response element operably linked to a nucleotide sequence encoding an anti-inflammatory cytokine, e.g., IL-4, IL-6, IL-10, IL-11, IL-13)(or encoding a chemokine such as MCP-1 or SDF-1, or encoding a growth factor such as TGF-beta, VEGF, or FGF) to a cell (e.g., to a cell in an individual).

Contacting a target cell can include administering a viral vector (e.g., a lentivirus, an AAV particle (virion)) to an individual. Virions (e.g., AAV virions) can be administered to a subject using in vivo or in vitro transduction techniques. If transduced in vitro or ex vivo a desired recipient cell (e.g., an MSC) can be removed from the individual, treated to introduce a subject heterologous nucleic acid, and reintroduced into the individual. Virions (e.g., AAV virions) can be formulated into pharmaceutical compositions and will can be administered using any convenient route, e.g., parenterally (e.g., administered via an intramuscular, subcutaneous, intratumoral, transdermal, intrathecal, intravenous, etc.).

As noted above for administration of cells, dosage treatment may be a single dose schedule or a multiple dose schedule. Moreover, the subject may be administered as many doses as appropriate. One of skill in the art can readily determine an appropriate number of doses.

For further elaboration of general techniques useful in the practice of this disclosure, the practitioner can refer to standard textbooks and reviews in cell biology, tissue culture, and embryology. With respect to tissue culture and stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

Kits

Also provided are kits for use in the subject methods. The subject kits include any combination of components, including but not limited to: (a) a subject nucleic acid (one that includes an NFκB inflammation response element operably linked to a nucleotide sequence encoding an anti-inflammatory cytokine, e.g., IL-4, IL-6, IL-10, IL-11, IL-13) (or encoding a chemokine such as MCP-1 or SDF-1, or encoding a growth factor such as TGF-beta, VEGF, or FGF); (b) an MSC or a population of MSCs; and (c) an MSC, or a population of MSCs, that includes a subject nucleic acid, e.g., present extrachromosomally or integrated into its genome.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-21 (SET A) and 1-24 (SET B) are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A

1. A nucleic acid comprising an NFκB inflammation response element operably linked to a nucleotide sequence encoding IL-4.
2. The nucleic acid of 1, wherein the nucleic acid is an expression vector.
3. The nucleic acid of 2, wherein the expression vector is selected from: a linear expression vector, a circular expression vector, a plasmid, and a viral expression vector.
4. The nucleic acid of 1, wherein the expression vector is a viral expression vector.
5. The nucleic acid of any one of 2-4, wherein the expression vector is a lentiviral vector.
6. A cell comprising the nucleic acid of any one of 1-5.
7. The cell of 6, wherein said nucleic acid is integrated into the cell's genome.
8. The cell of 6 or 7, wherein the cell is a mesenchymal stem cell.
9. A mesenchymal stem cell (MSC) comprising a heterologous nucleic acid comprising an NFκB inflammation response element operably linked to a nucleotide sequence encoding an anti-inflammatory cytokine selected from: IL-4, IL-6, IL-11, and IL-13.
10. The MSC of 9, wherein the anti-inflammatory cytokine is IL-4.
11. The MSC of 9 or 10, wherein the heterologous nucleic acid is selected from: a linear expression vector, a circular expression vector, a plasmid, and a viral expression vector.
12. The MSC of any one of 9-11, wherein the heterologous nucleic acid is a viral expression vector.
13. The MSC of any one of 9-12, wherein the heterologous nucleic acid is a lentiviral vector.
14. The MSC of any one of 9-13, wherein the heterologous nucleic acid is integrated into the MSC's genome.
15. A method of treating an individual having an inflammation-associated ailment, the method comprising:
administering a mesenchymal stem cell (MSC) to the individual, wherein the MSC comprises a heterologous nucleic acid comprising an NFκB inflammation response element operably linked to a nucleotide sequence encoding an anti-inflammatory cytokine selected from: IL-4, IL-6, IL-10, IL-11, and IL-13.
16. The method of 15, wherein the anti-inflammatory cytokine is selected from: IL-4, IL-6, IL-11, and IL-13.
17. The method of 15 or 16, wherein the anti-inflammatory cytokine is IL-4.
18. The method of any one of 15-17, wherein the heterologous nucleic acid is selected from: a linear expression vector, a circular expression vector, a plasmid, and a viral expression vector.
19. The method of any one of 15-18, wherein the heterologous nucleic acid is a viral expression vector.
20. The method of any one of 15-19, wherein the heterologous nucleic acid is a lentiviral vector.
21. The method of any one of 15-20, wherein the heterologous nucleic acid is integrated into the MSC's genome.
22. The method of any one of 15-21, wherein the individual has chronic inflammation.
23. The method of any one of 15-22, wherein the individual has one or more of: a bone injury, osteoarthritis, rheumatoid arthritis, a cardiovascular disease, hepatic inflammation, a myocardial infarction, musculoskeletal inflammation, neurological associated inflammation, diabetes, and a spinal cord injury.
24. The nucleic acid, cell, MSC, or method of any of 1-23, wherein the NFκB inflammation response element includes the nucleotide sequence set forth in SEQ ID NO: 1.

Set B

1. A nucleic acid comprising an NFκB inflammation response element operably linked to a nucleotide sequence encoding a chemokine (e.g., selected from Table 1, or selected from MCP-1 and SDF-1) or a growth factor (e.g., selected from TGF-beta, VEGF, and FGF—e.g., see suitable examples for TGF-beta, VEGF, and FGF listed above in the "Nucleic Acids" section).
2. The nucleic acid of 1, wherein the nucleic acid is an expression vector.
3. The nucleic acid of 2, wherein the expression vector is selected from: a linear expression vector, a circular expression vector, a plasmid, and a viral expression vector.
4. The nucleic acid of 1, wherein the expression vector is a viral expression vector.
5. The nucleic acid of any one of 2-4, wherein the expression vector is a lentiviral vector.
6. A cell comprising the nucleic acid of any one of 1-5.
7. The cell of 6, wherein said nucleic acid is integrated into the cell's genome.
8. The cell of 6 or 7, wherein the cell is a mesenchymal stem cell.
9. A mesenchymal stem cell (MSC) comprising a heterologous nucleic acid comprising an NFκB inflammation response element operably linked to a nucleotide sequence encoding a chemokine or a growth factor.
10. The MSC of 9, wherein the chemokine is selected from Table 1, or selected from: MCP-1 and SDF-1; and wherein the growth factor is selected from: TGF-beta, VEGF, and FGF (see e.g., suitable examples for TGF-beta, VEGF, and FGF listed above in the "Nucleic Acids" section).
11. The MSC of 9 or 10, wherein the heterologous nucleic acid is selected from: a linear expression vector, a circular expression vector, a plasmid, and a viral expression vector.
12. The MSC of any one of 9-11, wherein the heterologous nucleic acid is a viral expression vector.
13. The MSC of any one of 9-12, wherein the heterologous nucleic acid is a lentiviral vector.
14. The MSC of any one of 9-13, wherein the heterologous nucleic acid is integrated into the MSC's genome.
15. A method of treating an individual having an inflammation-associated ailment, the method comprising:
administering a mesenchymal stem cell (MSC) to the individual, wherein the MSC comprises a heterologous nucleic acid comprising an NFκB inflammation response element operably linked to a nucleotide sequence encoding a chemokine or a growth factor.
16. The method of 15, wherein the chemokine is selected from Table 1, or selected from: MCP-1 and SDF-1.
17. The method of 15 or 16, wherein the growth factor is selected from: TGF-beta, VEGF, and FGF (see e.g., suitable examples for TGF-beta, VEGF, and FGF listed above in the "Nucleic Acids" section).
18. The method of any one of 15-17, wherein the heterologous nucleic acid is selected from: a linear expression vector, a circular expression vector, a plasmid, and a viral expression vector.

19. The method of any one of 15-18, wherein the heterologous nucleic acid is a viral expression vector.
20. The method of any one of 15-19, wherein the heterologous nucleic acid is a lentiviral vector.
21. The method of any one of 15-20, wherein the heterologous nucleic acid is integrated into the MSC's genome.
22. The method of any one of 15-21, wherein the individual has chronic inflammation.
23. The method of any one of 15-22, wherein the individual has one or more of: a bone injury, osteoarthritis, rheumatoid arthritis, a cardiovascular disease, hepatic inflammation, a myocardial infarction, musculoskeletal inflammation, neurological associated inflammation, diabetes, and a spinal cord injury.
24. The nucleic acid, cell, MSC, or method of any of 1-23, wherein the NFκB inflammation response element includes the nucleotide sequence set forth in SEQ ID NO: 1.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (ph; seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

An NF-κB responsive IL-4-expression lentiviral vector was generated, and was transduced into murine bone marrow-derived mesenchymal stem cells (MSCs). The IL-4 secretion profiles in the MSCs exposed to inflammatory stimuli, and the ability to modulate macrophage polarization status were examined. This example shows that NFκB sensing / anti-inflammatory secreting (e.g., IL-4 secreting) MSCs can modulate inflammatory macrophages into a favorable anti-inflammatory phenotype in response to an inflammatory environment.

Materials and Methods

Mouse bone marrow cells were collected from femurs and tibias of C57BL/6 male mice (8-10 weeks of age). Institutional guidelines for the care and use of laboratory animals was observed in all aspects of this project. The constitutive IL-4 expression lentivirus driven by CMV promoter was generated from the IL-4 expression plasmid pCMV3-mIL-4 (Sino Biological Inc.), and ligated into the CD511B-1 lentiviral expression vector (System Biosciences). The NFκB sensing IL-4 secretion vector (nucleotide sequence encoding IL-4 operably linked to an NFκB inflammation response element) was generated from the reporter plasmid pGL4.32 [luc2/NF-κB-RE/Hygro] (Promega), and replaced the CMV promoter on the lentiviral vector. The fragment containing the NF-κB inflammation response element and a mini-promoter was amplified by PCR (Forward primer: 5'-tacgt-cactagttgagctcgct-3' (SEQ ID NO: 24), Reverse primer: 5'-atgctaggtaccggtggcttta-3' (SEQ ID NO: 25)) from the reporter plasmid pGL4.32[luc2/NF-κB-RE/Hygro] (Promega) using Phusion high-fidelity DNA polymerase (NEB), and replaced the CMV promoter on the pCMV3-mIL-4 to generated pNFκBRE-mIL-4 vector. The successful construct was confirmed by sequencing (McLab). The NF-κB sensing and IL-4 expression fragment was released from pNFκBRE-mIL-4 (SpeI/NotI) and ligated into the CD511B-1 vector to generate the pCDH-NFκBRE-mIL-4-copGFP vector.

Mouse bone marrow MSCs were infected with the virus vectors (MOI=40), and the infection efficiency was confirmed by the EGFP expression under fluorescence microscope. The IL-4 secretion induced by endotoxin (1 μg/ml lipopolysaccharide, LPS) or untreated control was quantified by ELISA (Biolegend) (FIG. 1). The cell viability was evaluated by Pico-green assay (Invitrogen). Primary macrophages were then treated by the MSC conditioned media containing LPS and the induced IL-4 secretion (FIG. 2), and the macrophage polarization status was evaluated by quantitative PCR and ELISA.

Results

The IL-4 secretion in NFκB sensing MSCs was significantly induced by LPS exposure for 24 hours (from 172.18 to 3679.95 pg/ml, FIG. 1a). No significant difference was observed in the constitutive IL-4 secreting or control MSCs exposed to LPS. This demonstrates that MSCs harboring a nucleic acid encoding a nucleotide sequence encoding an anti-inflammatory cytokine operably linked to an NFκB inflammation response element, secret the anti-inflammatory cytokine (e.g., IL-4, IL-6, IL-10, IL-11, and IL-13) in response to an inflammatory signal (e.g., LPS). The IL-4 secretion in NFκB sensing MSCs was decreased to 487.98 pg/ml one day after LPS was withdrawn (day 2), and reduced to basal levels (170.88 pg/ml) at day 3 (FIG. 1b), demonstrating the responsiveness of the NFκB inflammation response element (e.g., reversibility—expression decreases after removal of stimulus). The IL-4 secretion was increased to 28797.00 pg/ml when the NFκB activity in MSCs was induced again by LPS at day 5. Comparably, the IL-4 secretion in NFκB sensing MSCs with continuous LPS exposure was decreased at day 2 (1028.45 pg/ml) and day 3 (1379.45 pg/ml), and increased after day 4 (5094.65 pg/ml, FIG. 1c).

FIG. 1a-1c The secretion profile of NF-κB sensing and IL-4 secreting MSCs in response to LPS. The IL-4 secretion in response to LPS in genetically modified or control MSCs (FIG. 1a), or in NF-κB sensing MSCs with intermittent (FIG. 1b) or continuous (FIG. 1c) LPS exposure were quantified by ELISA. *p<0.05, p<0.01, *p<0.005

Importantly, the IL-4 secreted by NFκB sensing or constitutive active MSCs was able to modulate inflammatory M1 macrophages (TNFα+, iNOS+, TNFα/IL1Ra high) into an anti-inflammatory M2 macrophage (Arg1+/CD206+) phenotype at both mRNA and protein expression levels (FIG. 2).

Figure 2B:
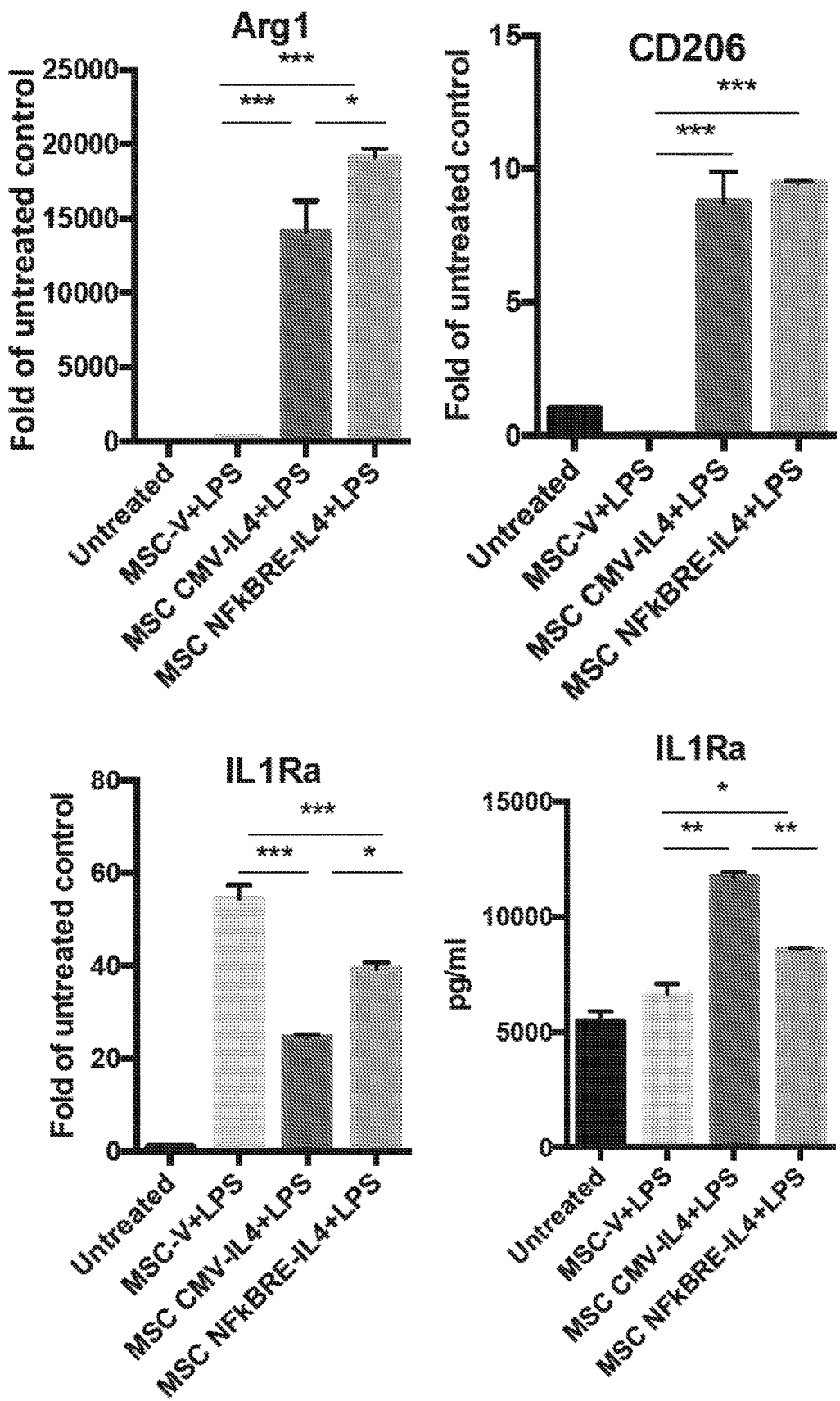

FIG. 2a-2b. Modulation of macrophage polarization by constitutive or NF-κB sensing IL-4 secreting MSCs in response to LPS. The conditioned media collected from genetically modified or control MSCs exposed to LPS were used to treat mouse primary macrophages. M1 (FIG. 2a) and M2 (FIG. 2b) macrophage markers were quantified by PCR and ELISA. *p<0.05, p<0.01, *p<0.005

Example 2

NF-κB Sensing and IL-4 Secreting Mesenchymal Stromal Cells as an "On-Demand" Drug Delivery System to Modulate Inflammation The data provided herein demonstrate the generation of NF-κB responsive, or constitutively active, IL4-expression lentiviral vectors transduced into murine bone marrow-derived mesenchymal stromal cells (MSCs). MSCs with a constitutively active IL-4 expression vector produced large quantities of IL-4 continuously whereas IL-4 secretion was significantly induced by lipopolysaccharide (LPS) in the NF-κB sensing MSCs. In contrast, LPS had no effect on MSCs with IL-4 secretion driven by a constitutively active promoter. Intermittent and continuous LPS treatment displayed distinct NF-κB activation profiles, and this regulation was independent of IL-4 signaling. The supernatant containing IL-4 from the LPS treated MSCs suppressed M1 marker (iNOS and TNFα) expression and enhanced M2 marker (Arginase 1, CD206, and IL1Ra) expression in primary murine macrophages. The IL-4 secretion at the basal, non-LPS induced level was sufficient to suppress TNFα and enhance Arginase 1 at a lower level, but had no significant effects on iNOS, CD206, and IL1Ra expression. Finally, IL-4 secretion at basal or LPS-induced levels significantly suppressed osteogenic differentiation of MSCs. The findings presented herein suggest that the IL-4 secreting MSCs driven by NF-κB sensing or constitutive active promoter are useful for mitigating the effects of chronic inflammation and promoting earlier tissue regeneration.

The aim of this study was to develop MSCs as "on-demand" drug delivery vehicles that have an enhanced ability to modulate macrophage phenotype towards tissue-regenerative M2 when these cells are implanted into an inflammatory microenvironment. To this end, an IL-4 transgene was placed under the promoter region of an inflammatory transcription factor NF-κB. As a result, these cells produced IL-4 when NF-κB was activated by inflammatory signals (such as inflammatory cytokines and toll-like receptor ligands) in the local microenvironment; once the inflammatory signaling was withdrawn, IL-4 production quickly ceased, limiting potential adverse effects. As an alternative approach MSCs that continuously produced IL-4 were created by placing the IL-4 transgene under the control of the constitutively active promoter region. These cell produced herein can be useful for cell based tissue engineering as well as the treatment of a wide variety of conditions in which limiting chronic inflammation and induction of tissue regenerative M2 macrophage polarization is beneficial.

Materials and Methods

Isolation of Murine Mesenchymal Stromal Cells and Macrophages

The method of isolating mouse bone marrow derived MSCs and macrophage has been described previously. In brief, bone marrow was collected from the femurs and tibias of 8-10 weeks old C57BL/6J male mice. Institutional Animals Care and Use Committee (IACUC) guidelines for the care and use of laboratory animals were observed in all aspects of this project. For MSC isolation, the cells were carefully suspended and passed through a 70 μm strainer, spun down, and resuspended in α-MEM (Thermo Scientific) supplied with 10% MSC certified (with enhanced clonal expansion efficiency) fetal bovine serum (FBS, Invitrogen) and antibiotic antimycotic solution (100 units of penicillin, 100 μg of streptomycin, and 0.25 μg of Amphotericin B per ml; Hyclone, Thermo Scientific). The fresh media was replaced the next day to remove the unattached cells (passage 1). The immunophenotype of isolated MSCs (CD105+/CD73+/CD90.2+/Sca1+CD45−/CD34−CD11b−, FIG. 8) as defined by International Society for Cell Therapy (ISCT) was characterized by LSR II flow cytometer (BD Bioscience) at passage 4. For macrophage isolation, the bone marrow cells were washed 3 times with culture medium (RPMI1640 medium supplemented with 10% heat inactivated FBS, and the antibiotic/antimycotic solution), re-suspended in the culture medium containing 30% of L929 cells conditioned medium and 10 ng/ml mouse macrophage colony stimulation factor (M-CSF, R & D), and re-plated in T-175 culture flasks at a concentration of $4\times10^7$ cells per flask. Cells were allowed to expand for 5-7 days, with a medium change at the second day to remove non-adherent cells. The cells were analyzed for macrophage surface marker expression (F4/80 & CD11b, Biolegend) after day 7.

Construction of IL-4 Expressing Plasmids

The constitutive IL-4 expression lentivirus driven by Cytomegalovirus (CMV) promoter was released from the IL-4 expression plasmid pCMV3-mIL4 (Sino Biological Inc.) by digested with SpeI/NotI restriction enzyme and ligated into the pCDH-CMV-copGFP lentiviral expression vector (CD511B-1, System Biosciences) to generate the pCDH-CMV-mIL4-copGFP vector. The fragment containing the NF-KB response element and a mini-promoter was amplified by PCR (Forward primer: 5'-tacgtcactagtt-gagctcgct-3', Reverse primer: 5'-atgctaggtaccggtggcttta-3') from the reporter plasmid pGL4.32[luc2/NF-κB-RE/Hygro] (Promega) using Phusion high-fidelity DNA polymerase (NEB), and replaced the CMV promoter on the pCMV3-mIL4 to generated pNFκBRE-mIL4 vector. The successful construct was confirmed by Sanger DNA sequencing (McLab). The NF-κB sensing and IL-4 expression fragment was released from pNFκBRE-mIL4 (SpeI/NotI, NEB) and ligated into the CD511B-1 vector to generate the pCDH-NFκBRE-mIL4-copGFP vector.

Preparation and Infection of Lentiviral Vectors

The virus preparation was performed as previously described. Human embryonic kidney 293T cells (ATCC, Manassas, Va.) were cultured in Dulbecco's modified eagle medium (Life Technologies, Pleasanton, Calif.) supplied with 10% heat inactivated fetal bovine serum (FBS, Invitrogen, Waltham, Mass.) and antibiotic-antimycotic solution (100 units of penicillin, 100 μg of streptomycin, and 0.25 μg of Amphotericin B per ml; Hyclone, Thermo Scientific, Waltham, Mass.). Human immunodeficiency virus-1 based vesicular stomatitis virus-G (VSV-G) pseudotype lentivirus particles were generated by co-transfecting the IL-4 expressing lentivirus vector, psPAX2 packaging vector, and pMD2G VSV-G envelope vector into 293T cells using calcium phosphate transfection kit (Clontech, Mountain View, Calif.) with 25 μM chloroquine. The culture supernatant was collected 48 h post-transfection and the cellular debris was removed by centrifugation. The virus titer was determined by using 293T cells; the titer of multiplicity of infection (MOI) on 293T cells were used to calculate the virus amount used in MSC infection. The supernatant was mixed with MSC culture medium at 1:1 ratio and supplemented with 6 μg/ml of polybrene (Sigma Aldrich), and infected to murine MSCs at MOI=40. The infection efficiency (number of GFP+ cells) was confirmed by LSRII flow cytometer (BD) 4 days post-infection. Flow cytometry analysis was done on instruments in Stanford Shared FACS Facility.

Induction of IL-4 Secretion in MSCs and Macrophage Polarization

Figure 5A:
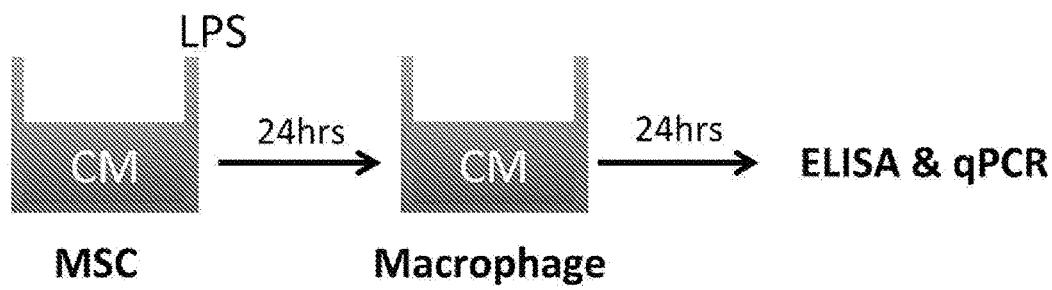
Figure 5B:
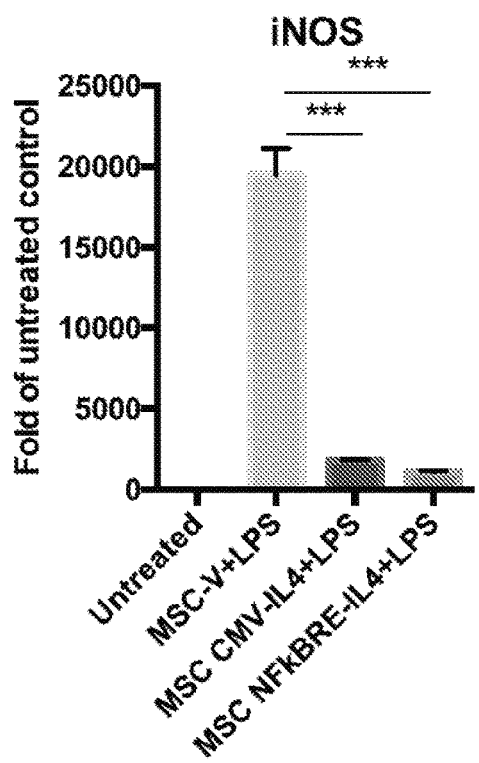
Figure 5C:
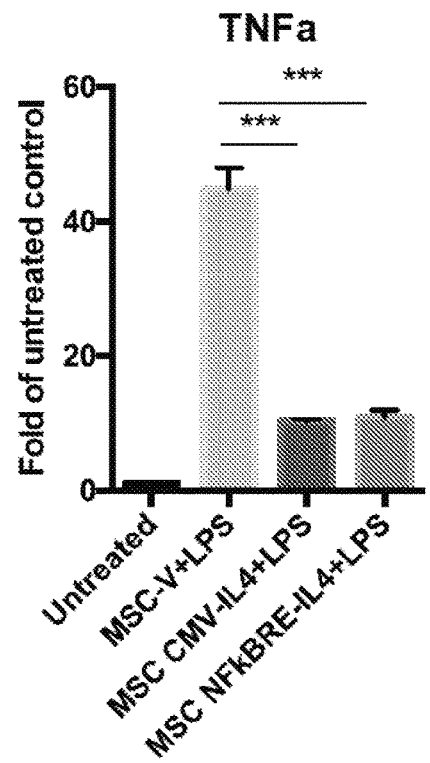
Figure 5D:
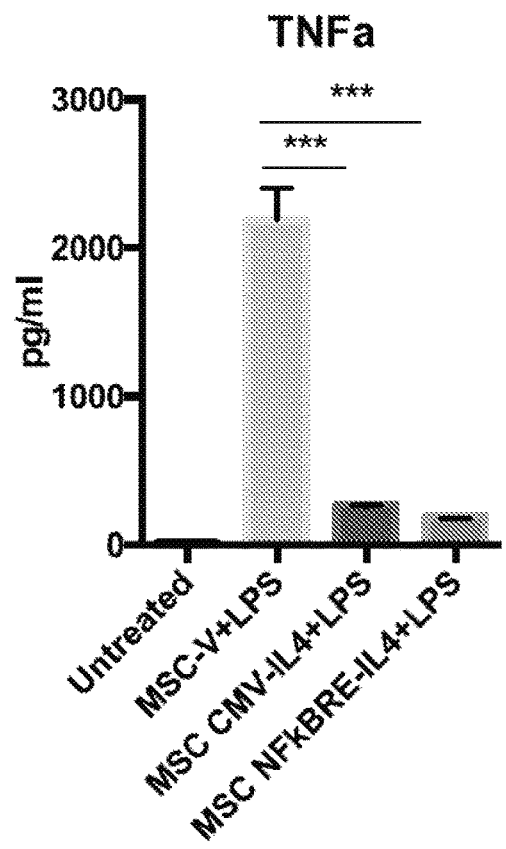
Figure 5E:
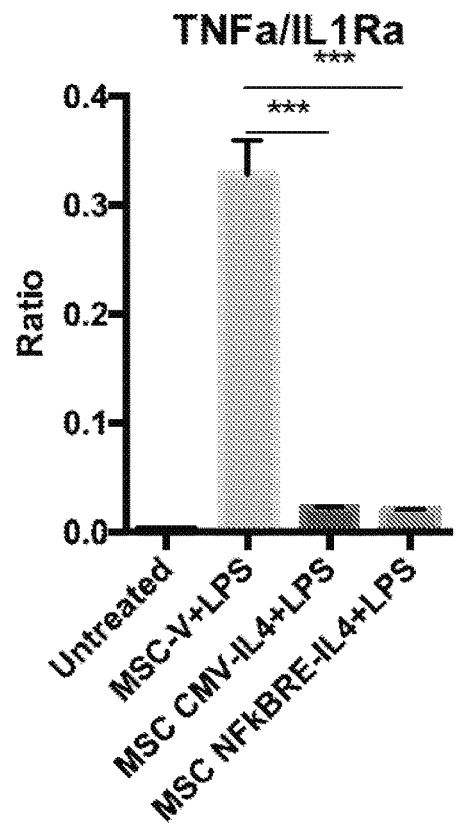
Figure 5F:
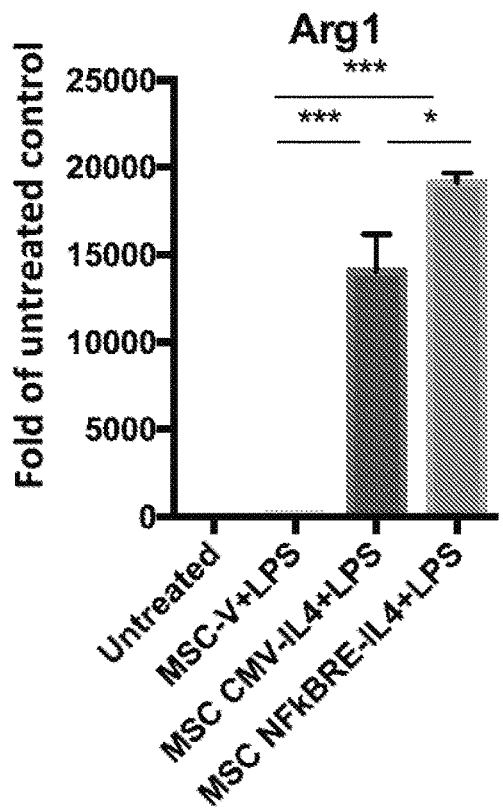
Figure 5G:
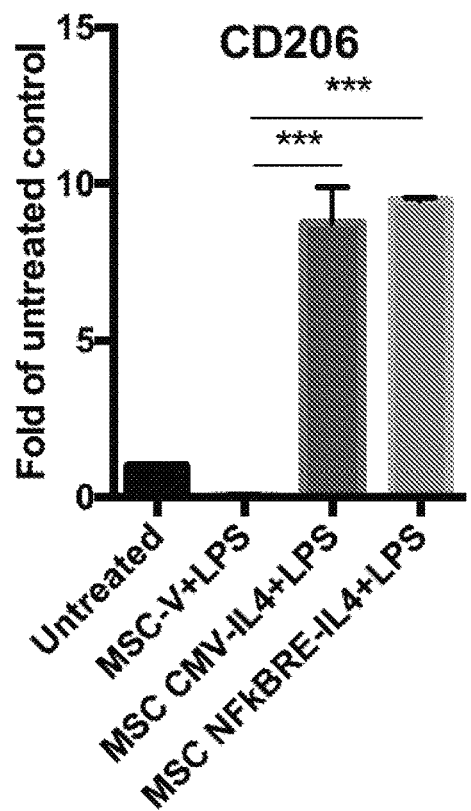
Figure 5H:
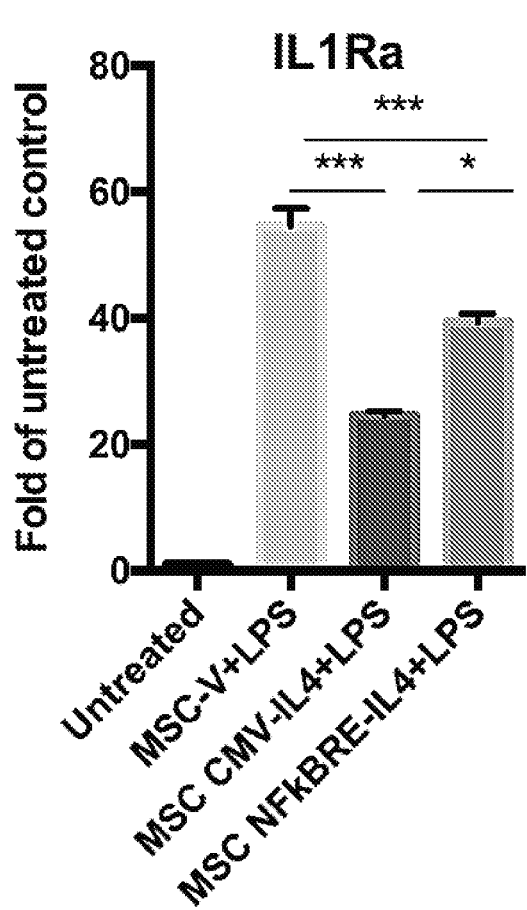
Figure 5I:
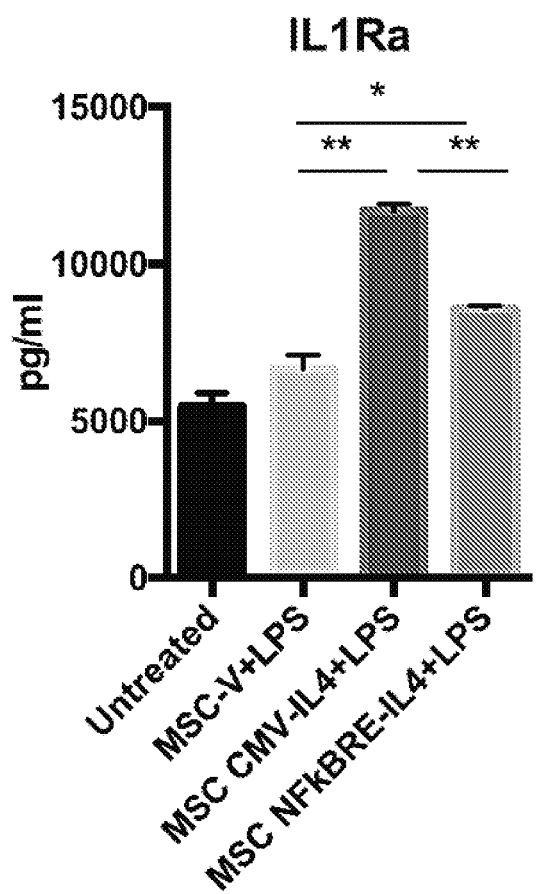
Figure 6A:
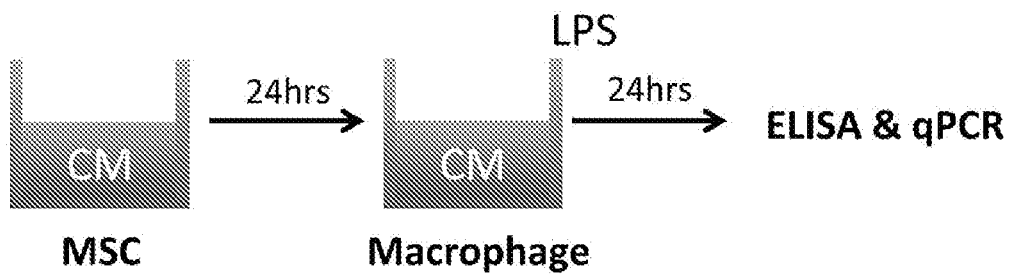
FIG. 6a-6i. $MSC^{NF-\kappa BRE\ IL4}$ exposed to LPS have comparable immunomodulation ability with constitutive IL4 secreting MSCs.
Figure 6B:
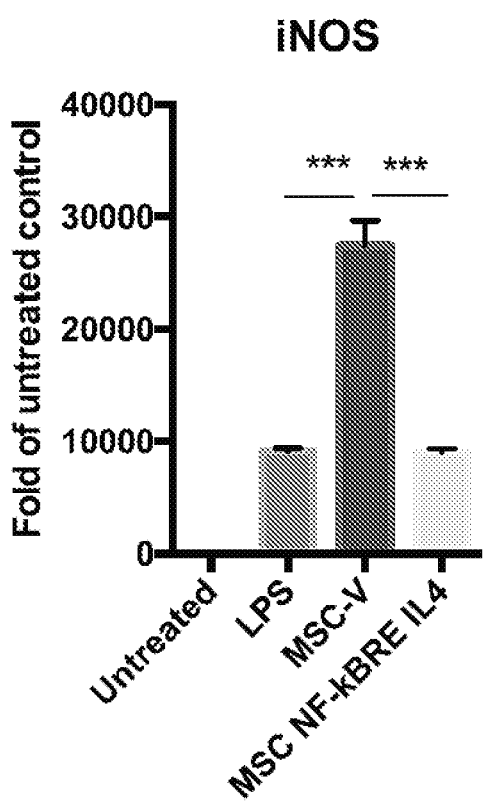
Figure 6C:
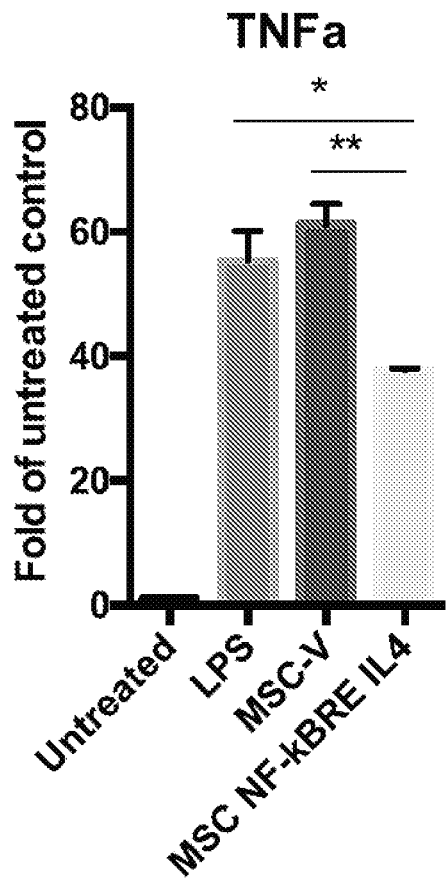
Figure 6D:
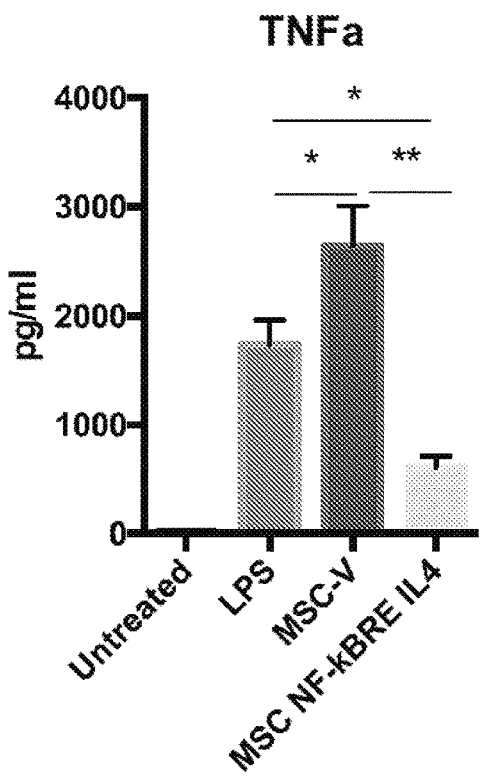
Figure 6E:
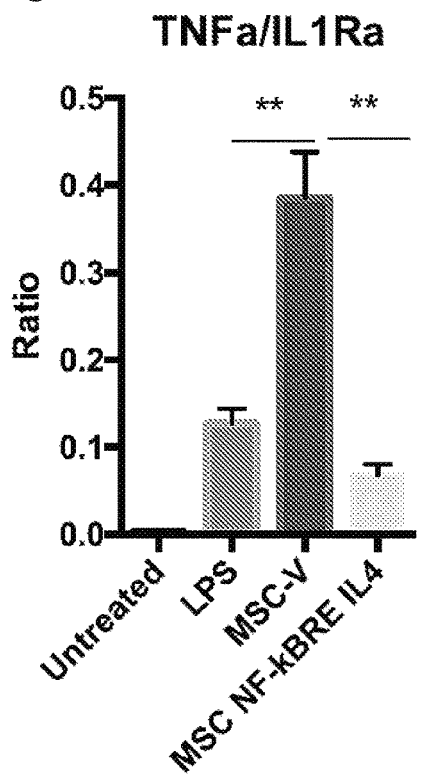
Figure 6F:
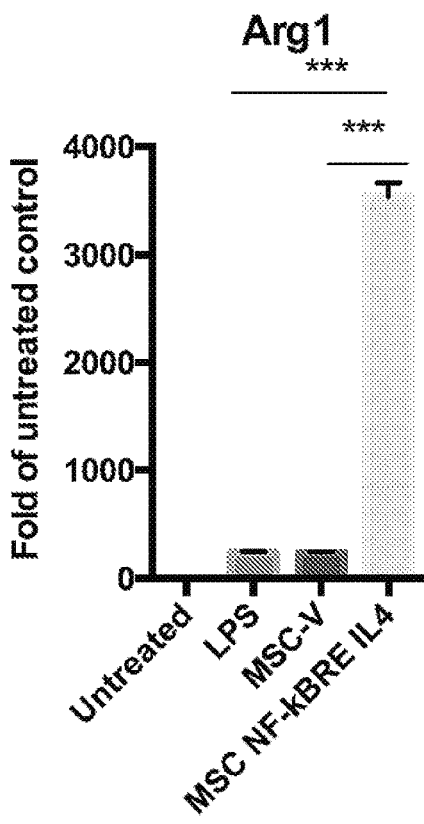
Figure 6G:
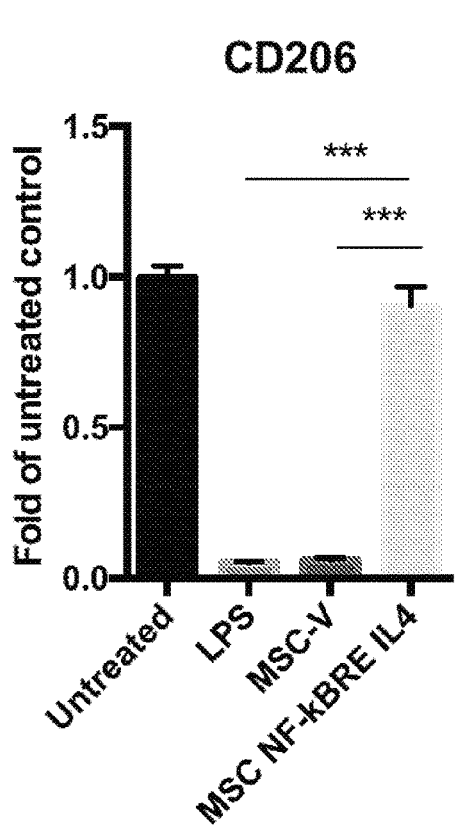
Figure 6H:
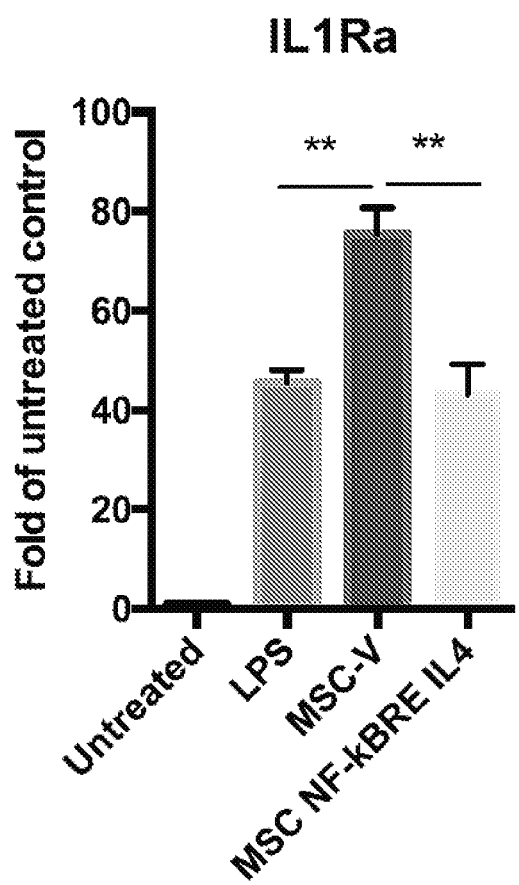
Figure 6I:
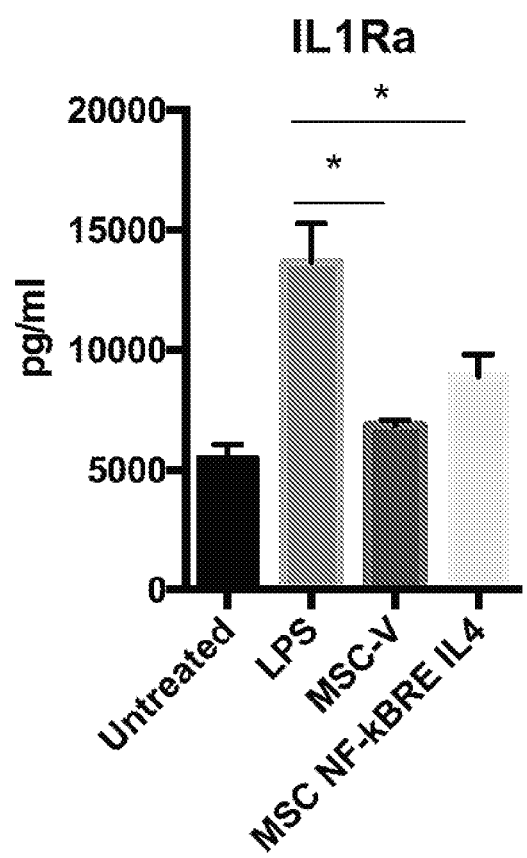

Lipopolysaccharide (LPS, from *Escherichia Coli* 0127: B8) was purchased from Sigma-Aldrich. The IL-4 secreting MSCs were exposed to 1 µg/ml LPS for 24 hours or left untreated. The LPS concentration was chosen following the protocols of previous studies investigating the effect of LPS on MSCs with the goal of reliably inducing NF-κB activation rather than modeling any specific disease state. Primary mouse macrophages were treated with the conditioned media containing LPS, or the conditioned media from untreated control but freshly added 1 µg/ml LPS (FIG. 5a & FIG. 6a). The macrophage polarization status 24 hours later was evaluated by quantitative real-time PCR and ELISA as described in following sections.

Enzyme Linked Immunosorbent Assay

Enzyme-linked immunosorbent assay (ELISA) kits for IL-4 and TNF-α ere purchased from Biolegend. IL1-Ra assay kit was purchased from R&D System. Manufacturers' protocols were followed carefully. The optical densities were determined using a Bio-Rad 3550-UV microplate reader (Bio-Rad, Hercules, Calif.) set at 450 nm.

Quantitative PCR

Cellular RNAs were extracted by using RNeasy RNA purification kit (Qiagen, Valencia, Calif.). RNAs were reverse transcribed into complementary DNA (cDNA) using a high-capacity cDNA archive kit (Applied Biosystems, Foster City, Calif.). Probes for 18s rRNA, TNF-α, IL1Ra, iNOS, Arginase1, and CD206 were purchased from Applied Biosystems. Reverse-transcriptase polymerase chain reaction (RT-PCR) was performed in an ABI 7900HT Sequencing Detection System (Applied Biosystems), using 18 s rRNA as the internal control. The $-\Delta\Delta Ct$ relative quantization method was used to evaluate gene expression level.

Luciferase Assay

The lentiviral NF-κB luciferase reporter vector (pCDH-NF-κB-luc2p-copEGFP) was generated previously. Murine MSCs were infected by the reporter viral vectors as described in the "preparation and infection of lentiviral vector" section. Cellular proteins were harvested and analyzed using a luciferase assay kit (Promega). The manufacturer's protocol was followed carefully. The results were normalized by total protein concentration as measured by Pierce® BCA protein assay kit (Thermo Scientific).

Osteogenesis Assay

IL-4 secreting mouse MSCs or control cells were grown in osteogenic medium (α-MEM (Thermo Scientific) supplemented with 10% FBS, 100 nM dexamethasone, 10 mM β-glycerol phosphate and 50 µM ascorbate-2-phosphate, Sigma) or control medium. The supernatants at week 2 were used for the alkaline phosphatase (ALP) activity assay (QuantiChrome™ Alkaline phosphatase assay kit, Cat. No. DALP-250; Bioassay Systems, Hayward, Calif.). Extracellular matrix mineralization in mouse MSCs was stained using the Alizarin red (Sigma) at week 3. The results were photographed and the staining was eluted by 10% cetylpyridinium chloride (Sigma) and quantified by measuring the absorbance at 562 nm.

Statistical Analysis

Non-paired t tests were performed for data with two groups, and a one-way ANOVA with Tukey's post-hoc test was performed for data with 3 or more groups. The statistical analysis was conducted using Prism 6 (GraphPad Software, San Diego, Calif.). Data are reported as mean±standard error of the mean. The osteogenesis assay was performed with six replicates. The luciferase assay was performed with four replicates. ELISA and quantitative PCR analysis was performed in triplicate. $P<0.05$ was chosen as the threshold of statistical significance.

Results

IL-4 Secretion in MSC Driven by NF-κB Sensing or Constitutive Active Promoters

Murine MSCs were infected with the lentiviral vectors to generate the vector control MSC ($MSC^V$, with pCDH-CMV-copGFP vector), NF-κB sensing and IL-4 secreting MSC ($MSC^{NF-\kappa BRE\ IL4}$, with pCDH-NF-κBRE-mIL4-copGFP vector), and constitutive IL-4 secreting MSC ($MSC^{CMV-IL4}$). The IL-4 secretion in mock-infected MSCs and $MSC^V$ was below the detectable range of ELISA, regardless of the presence or absence of 1 µg/ml LPS. IL-4 secretion in $MSC^{NF-\kappa BRE\ IL4}$ was significantly induced by LPS exposure for 24 h (from 172.18 to 3679.95 pg/ml, FIG. 3). $MSC^{CMV-IL-4}$ secreted high levels of IL-4 constitutively with no significant difference observed after exposure to LPS (19416.5 to 22291.0 pg/ml, FIG. 3).

Figure 4A:
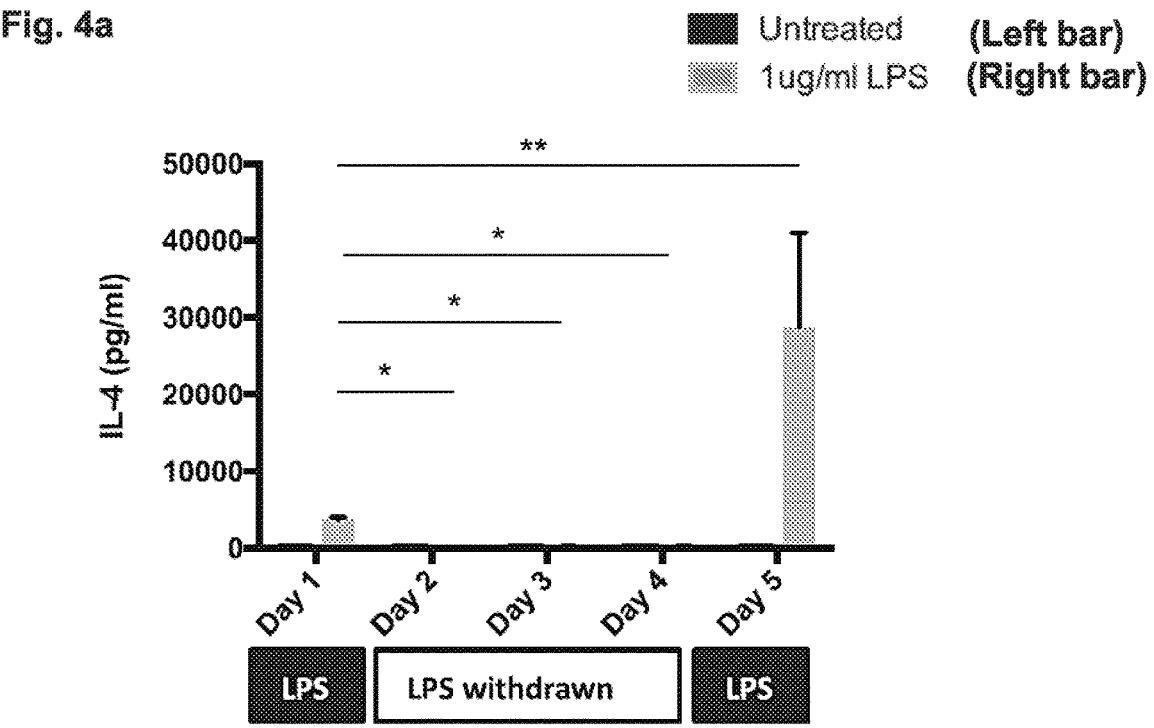
FIG. 4a-4d. Continuous or intermittent LPS administration displayed differential NF-κB activation and IL-4 secretion in MSC. NF-κB sensing and IL-4 secreting MSC was exposed to 1 μg/ml LPS intermittently at day1 and day5 (FIG. 4a) or continuously from day1 to day5 (FIG. 4b). The supernatants were collected daily and the IL-4 secretion was quantified by ELISA. The MSCs with NF-κB response luciferase reporter gene expression were exposed to 1 μg/ml LPS intermittently (FIG. 4c) or continuously (FIG. 4d), and the NF-κB activities were measured by luciferase assay. The difference between LPS treated group from day1-5 was analyzed by one-way ANOVA with multi-comparison test with day1 as control. *$p<0.05$, **$p<0.01$ FIG. 5a-5i. $MSC^{NF-\kappa BRE\ IL4}$ exposed to LPS have comparable immunomodulation ability with $MSC^{CMV\ IL4}$ (FIG. 5a) Illustration of IL-4 secreting MSC-mediated immunomodulation on macrophage polarization. The conditioned media collected from MSCs (vector, CMV-IL4, and NFκBRE-IL4) exposed to 1 µg/ml LPS were used to treat macrophages for 24 hours. M1 (FIG. 5b-5e) and M2 (FIG. 5f-5i) macrophage markers were analyzed by quantitative PCR (FIG. 5b, 5c, 5f, 5g, 5h) or ELISA (FIG. 5d, 5e, 5i). The ratio of TNFα and IL-1RA production was determined to highlight balance of pro- and anti-inflammatory factors (FIG. 5e) The difference between LPS treated groups was analyzed by one-way ANOVA. *p<0.05, p<0.01, *p<0.005
Figure 4B:
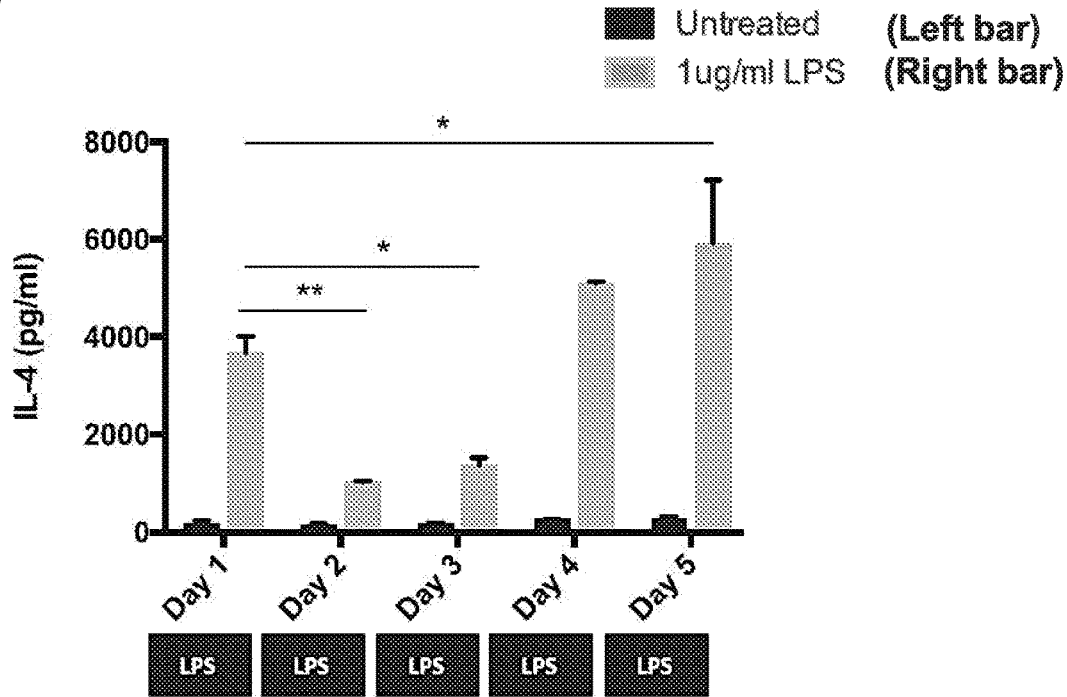
Figure 4C:
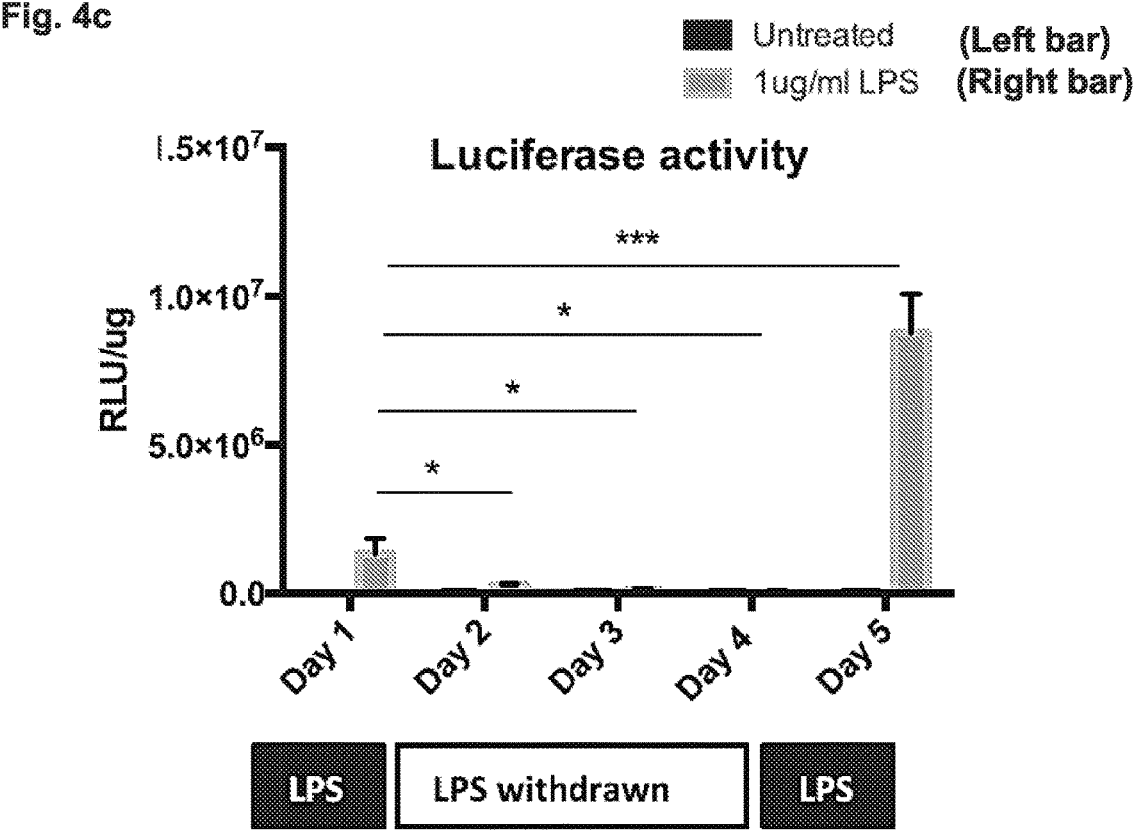
Figure 4D:
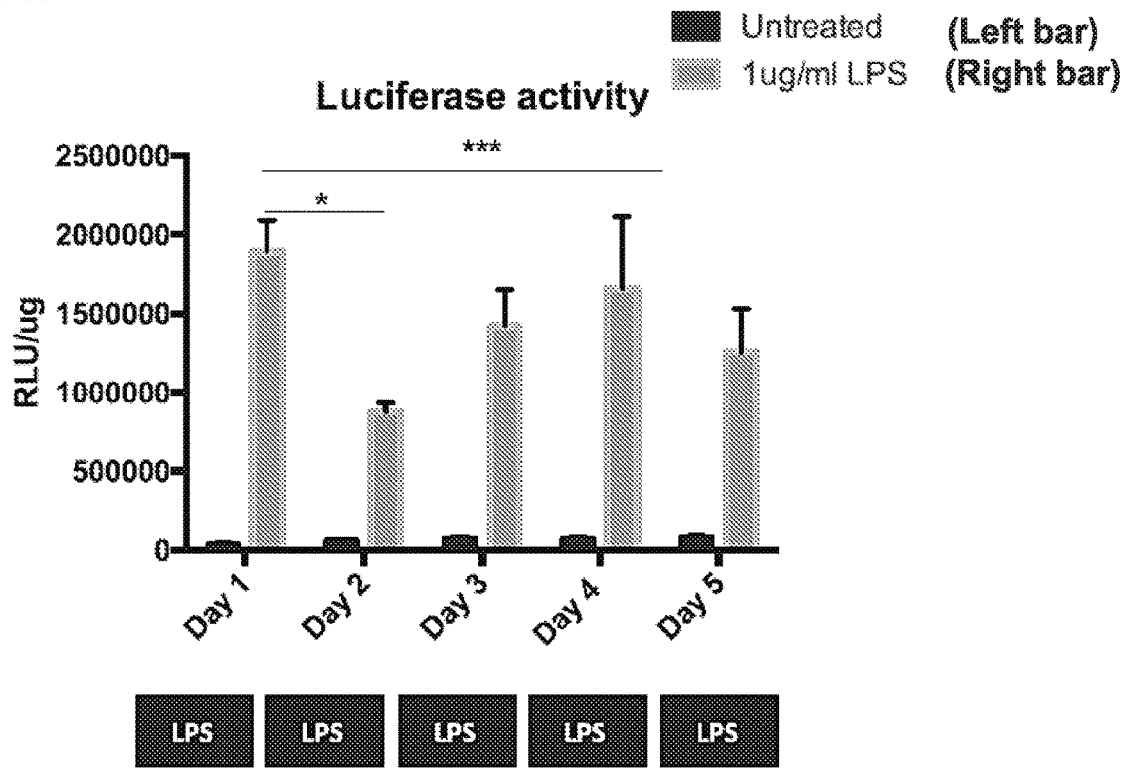

Intermittent and Continuous LPS Exposure Displayed Distinct NF-κB Activation Profiles in MSCs Next assessed was the effect of repeated NF-κB activation on the induction of IL-4 secretion from $MSC^{NF-\kappa BRE\ IL4}$ during which the cells were exposed to LPS either continuously or intermittently to simulate chronic and recurrent inflammatory conditions. The IL-4 secretion in $MSC^{NF-\kappa BRE\ IL4}$ was induced to 3679.95 pg/ml after one-day exposure to 1 µg/ml LPS. The secretion level was decreased to 487.98 pg/ml one day after LPS was withdrawn (day 2), and reduced to basal levels (170.88 pg/ml) at day 3 (FIG. 4a). The IL-4 secretion was increased to 28797.00 pg/ml when the NF-κB activity in MSCs was induced again by LPS at day 5 (FIG. 4a). Comparably, the IL-4 secretion in NF-κB sensing MSCs with continuous LPS exposure was decreased at day 2 (1028.45 pg/ml) and day 3 (1379.45 pg/ml), and increased again after day 4 (5094.65 pg/ml, FIG. 4b). To clarify whether IL-4 can affect the secretion profiles in $MSC^{NF-\kappa BRE\ IL4}$ exposed to LPS in an autocrine manner, MSCs were infected with NF-κB luciferase reporter lentivirus as previously described. The results showed that the NF-κB activation patterns induced by intermittent (FIG. 4c) or continuous (FIG. 4d) LPS treatment were consistent with the IL-4 secretion profiles in $MSC^{NF-\kappa BRE\ IL4}$, suggesting that IL-4 secretion did not alter the NF-κB activation status in $MSC^{NF-\kappa BRE\ IL4}$.

Macrophage Polarization by the Conditioned Media Containing IL-4

Figure 3:
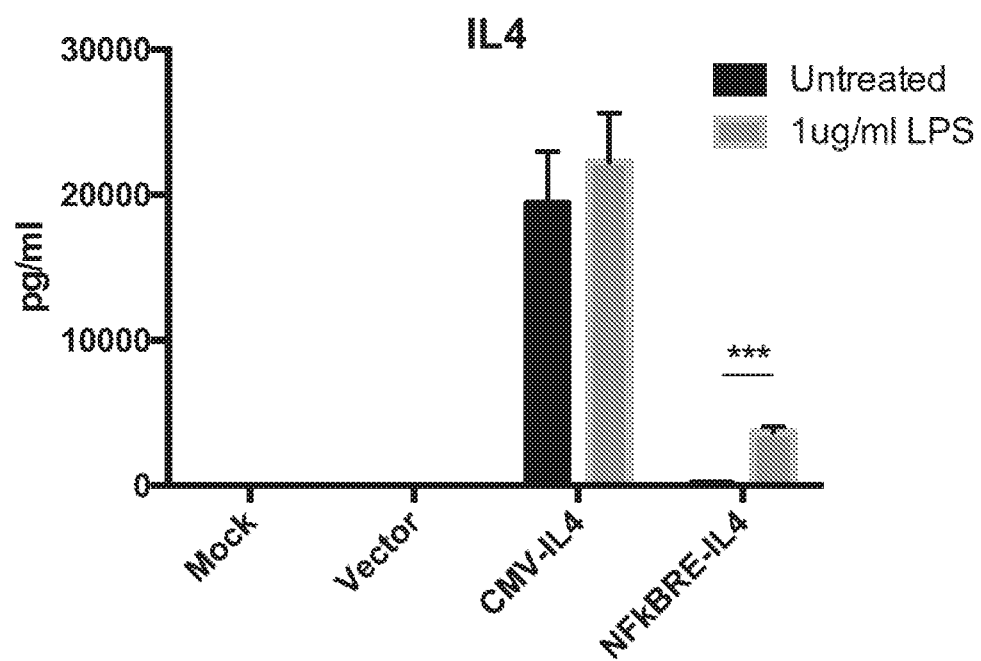
FIG. 3. Constitutive or NF-κB sensing IL-4 secretion by MSCs exposed to LPS. The $MSC^V$, $MSC^{CMV\ IL4}$, $MSC^{NF\kappa BRE\ IL4}$ or mock control was exposed to 1 μg/ml LPS for 24 hours or left untreated. IL-4 secretion was quantified by ELISA. The difference between LPS treated group and untreated control were compared. ***$p<0.005$.
Figure 9A:
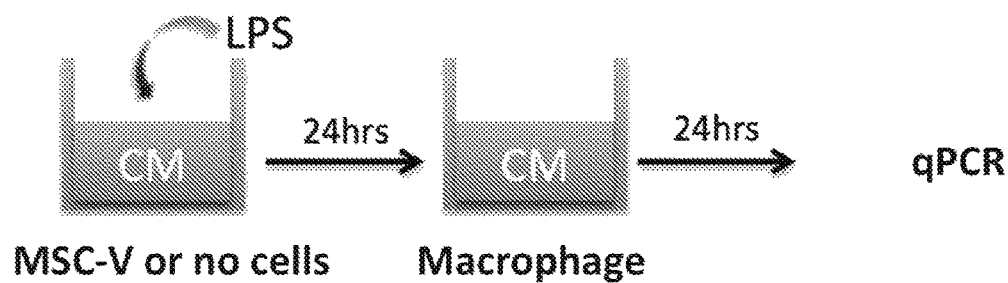
FIG. 9a-9g. $MSC^V$ exposed to LPS induced M1 macrophage marker expression and IL-10 secretion.
Figure 9B:
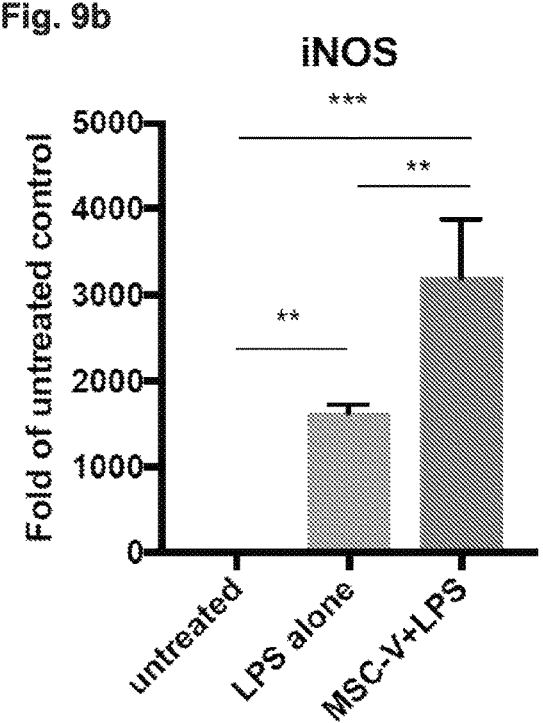
Figure 9C:
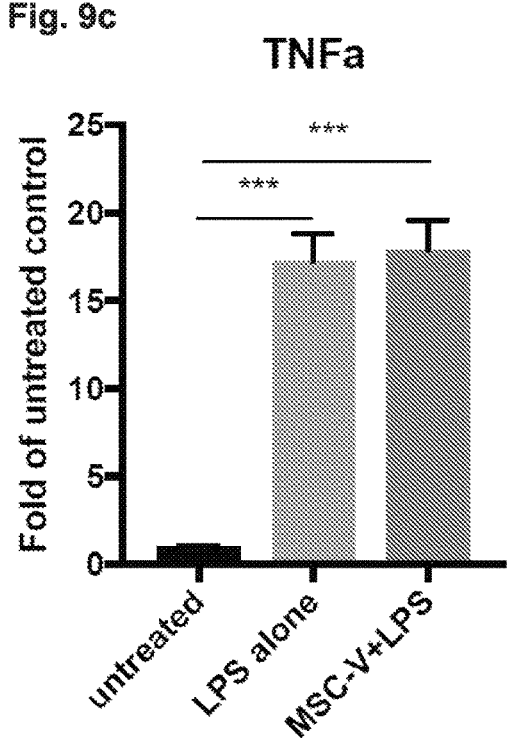
Figure 9D:
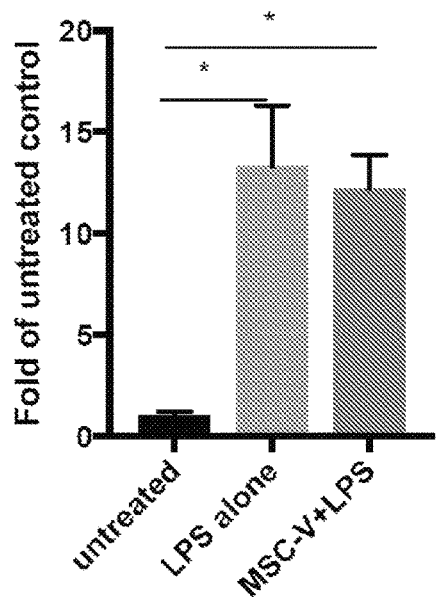
Figure 9E:
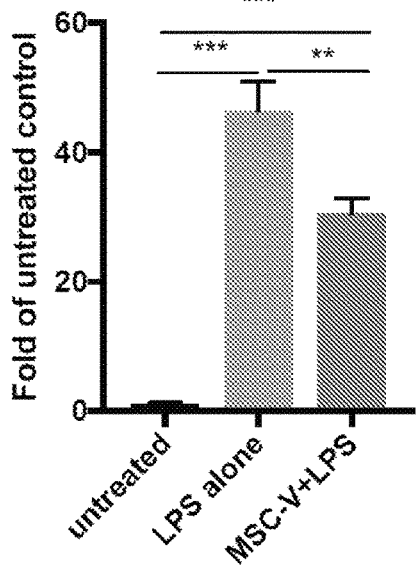
Figure 9F:
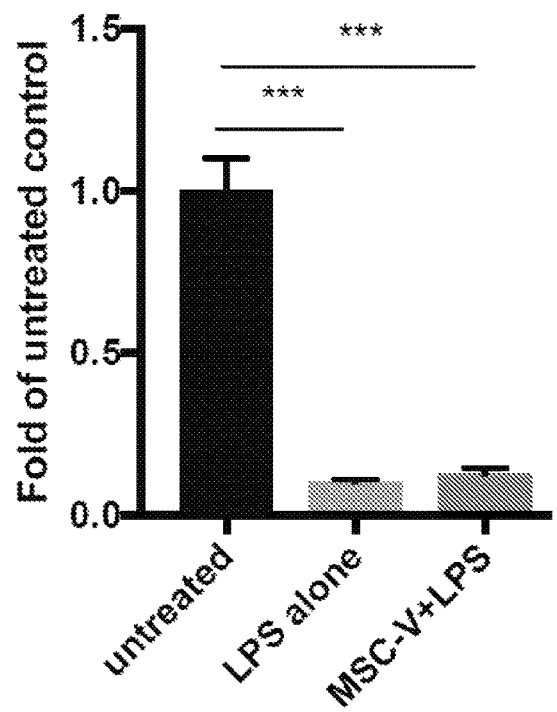
Figure 9G:
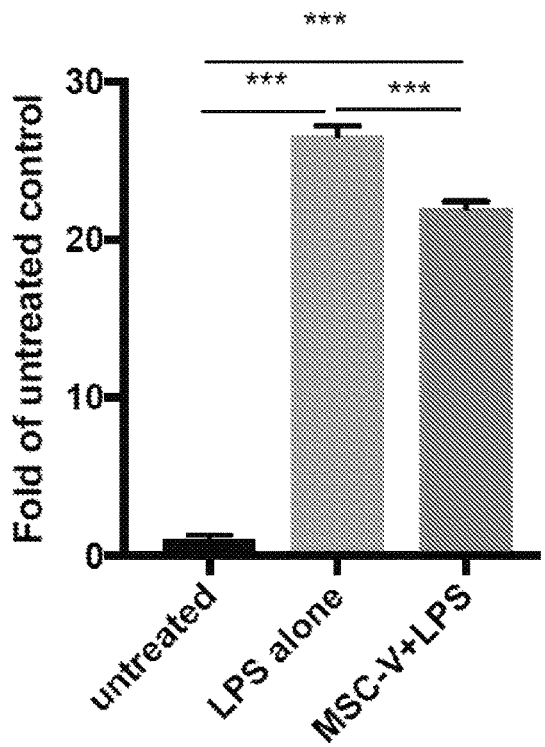

To examine the ability of MSC secreted IL-4 to modulate macrophage polarization, primary mouse macrophages were treated with the conditioned media from LPS exposed $MSC^V$, $MSC^{NF-\kappa BRE\ IL4}$ and $MSC^{CMV\ IL4}$ or left untreated (FIG. 5a). The conditioned media with 1 µg/ml LPS with no cells was collected to clarify the $MSC^V$ effects (FIG. 9a). Conditioned media from $MSC^V$ turned the primary macrophages into inflammatory M1 type cells (TNFα+, iNOS+, TNFα/IL1Ra high) due to remaining LPS in the media (FIG. 5b-5i). Conditioned media from $MSC^{NF-\kappa BRE\ IL4}$ and $MSC^{CMV\ IL4}$ was able to modulate this inflammatory M1 macrophage phenotype into an anti-inflammatory M2 macrophage (Arg1+/CD206+) phenotype at both mRNA and protein expression levels (FIG. 5b-5i). Notably, conditioned media from $MSC^{NF-\kappa BRE\ IL4}$ increased Arg1 (FIG. 5f) but decreased iNOS (FIG. 5b) and TNFα (FIG. 5d) expression compared to the $MSC^{CMV\ IL4}$ group, suggesting that $MSC^{NF-\kappa BRE\ IL4}$ has greater immunomodulation ability even though the IL-4 secretion levels were lower than that of MSC$^{CMV\ IL4}$ group (FIG. 3). In addition, conditioned media from MSC$^V$ increased iNOS, decreased Arg1 and IL-1Ra, and had no effect on TNF-α/IL-10/CD206 expression compared to the LPS alone (no cells) group (FIG. 9b-9g), suggesting that MSC$^V$ exposed to LPS may enhance inflammatory response in macrophages via paracrine regulation.

To assess the ability of untreated MSCs and the IL-4 secreted at baseline from unstimulated MSC$^{NF-\kappa BRE\ IL4}$ cells to modulate macrophage polarization, mouse macrophages were treated with conditioned media from untreated MSC$^V$ and MSC$^{NF-\kappa BRE}$ and freshly added 1 µg/ml LPS to induce M1 macrophage polarization (FIG. 6a). MSC culture media with or without LPS served as control groups. Conditioned media from MSC$^V$ did not mitigate the inflammatory phenotypes induced by LPS (FIG. 6b-6i), and even further enhanced iNOS expression (FIG. 6b) and TNFα/IL1Ra ratio (FIG. 6e) compared to the LPS treated macrophages. Interestingly the IL-4 secretion by MSC$^{NF-\kappa BRE\ IL4}$ at basal level (without NF-κB induction) was already able to modulate LPS-induced inflammatory M1 macrophages into an anti-inflammatory M2 macrophage phenotype at both mRNA and protein expression levels (FIG. 6b-6i). These effects, however, were less prominent than the ones caused by LPS induced IL-4 secretion by MSC$^{NF-\kappa BRE\ IL4}$ (FIG. 5).

Figure 7A:
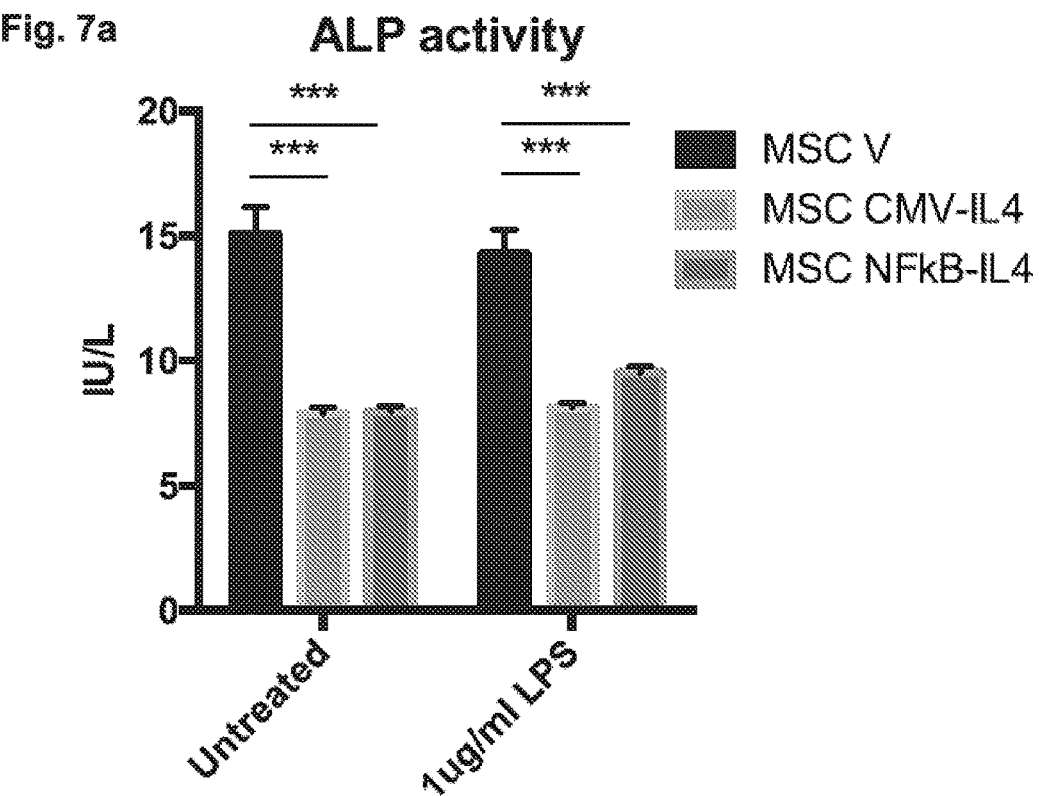
FIG. 7a-7b. IL-4 secretion inhibited osteogenesis in MSC. The osteogenic differentiation in IL-4 secreting MSCs was examined by (FIG. 7a) the ALP activity in the supernatant at week 2 and (FIG. 7b) calcium mineralization stained by alizarin red at week 3 of osteogenesis. MSCs were exposed to 1 µg/ml LPS to activate NF-κB signaling or left untreated during the osteogenesis. The difference between groups was analyzed by one-way ANOVA. ***p<0.005
Figure 7B:
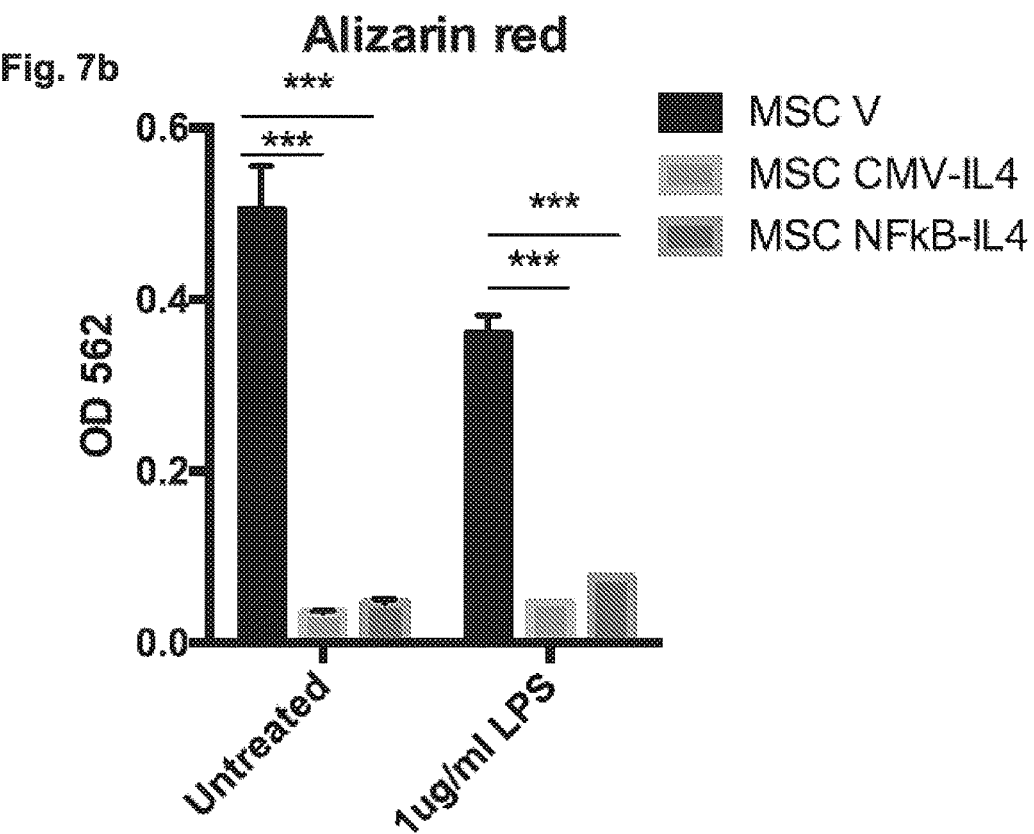

IL-4 Secretion Inhibited Osteogenesis in MSC$^{NF-\kappa BRE\ IL4}$ and MSC$^{CMV\ IL4}$ The osteogenic ability of IL-4 secreting MSCs at basal or induction level was examined in vitro. In the supernatants collected at week 2, ALP activities in MSC$^{NF-\kappa BRE\ IL4}$ and MSC$^{CMV\ IL4}$ were decreased compared to MSC$^V$. Continuous LPS treatment had no effects on ALP activity in MSCs (FIG. 7a). Similarly, the extracellular matrix mineralization in MCS$^{NF-\kappa BRE\ IL4}$ and MSC$^{CMV\ IL4}$ was decreased at week 3, and the results were not changed by LPS treatment (FIG. 7b).

Discussion

The experiments presented herein show that MSC$^{NF-\kappa BRE\ IL4}$ and MSC$^{CMV\ IL4}$ can secrete significant IL-4 and modulate inflammatory macrophages into a favorable anti-inflammatory phenotype. Using MSC$^{NF-\kappa BRE\ IL4}$ can mitigate chronic inflammation-associated diseases in bone and other tissues with reduced adverse effects compared to constitutively active IL-4, as the IL-4 secretion is limited to the periods of ongoing inflammation.

The NF-κB sensing MSC model presented herein has the advantage of secreting biologically relevant levels of immune-modulators in response to inflammatory stimuli, with the reaction quickly diminishing after the inflammatory stimulus has been discontinued. In addition, the reaction can be further induced by repeated NF-κB activation to mitigate recurrent and/or persisting inflammation. Therefore, the inducible MSC-based cellular therapy can preserve therapeutic efficiency but largely reduce potential adverse effects.

Administration of exogenous MSCs with enhanced immunomodulatory capabilities on macrophage polarization is an efficient strategy for the treatment of chronic inflammatory diseases. The amount of IL-4 secreted by both MSC$^{NF-\kappa BRE\ IL4}$ and MSC$^{CMV\ IL4}$ was relatively high compared, for instance, to activated TH2 cells and can thus be expected to have a biological effect both in vitro and in vivo. Indeed, the IL-4 secreted both by MSC$^{NF-\kappa BRE\ IL4}$ and MSC$^{CMV\ IL4}$ cells was very effective in modulating macrophage polarization even after exposure to relatively high amounts of LPS. The exact amount of IL-4 delivered can be further fine-tuned by optimizing the total number of cells implanted to the site of injury.

The data presented herein show that continuous LPS stimulation induced a transient negative feedback regulation of NF-κB activation, whereas intermittent LPS stimulation enhanced NF-κB responses in MSC (FIG. 4). This observation suggested that the protective mechanism in MSCs could be sensitized in response to the recurrent inflammatory stimulus. The strategy of modulating the MSC response can be applied to existing treatment strategies to enhance their therapeutic efficiency.

In conclusion, the NF-κB sensing and IL-4 secreting MSC-based cell therapy presented above can be used to treat chronic inflammatory diseases with unresolved inflammation. The innovative inflammation-inducible system can reduce the adverse effects and therefore improve the therapeutic efficiency and prognosis in translational applications.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A population of isolated mammalian mesenchymal stem cells (MSCs) each of which comprises a heterologous nucleic acid sequence comprising a nucleotide sequence encoding an anti-inflammatory cytokine operably linked to a nuclear factor kappa B (NFκB) inflammation responsive element, wherein the population is capable expressing the anti-inflammatory cytokine in an amount sufficient to modulate inflammatory M1 macrophages into an anti-inflammatory M2 macrophage phenotype, and further wherein the anti-inflammatory cytokine is interleukin 4 (IL-4).

2. The population of isolated mammalian MSCs of claim 1, wherein the heterologous nucleic acid sequence is selected from the group consisting of a linear expression vector, a circular expression vector, a plasmid, and a viral expression vector.

3. The population of isolated mammalian MSCs of claim 2, wherein the heterologous nucleic acid sequence is a lentiviral expression vector.

4. The population of isolated mammalian MSCs of claim 2, wherein the heterologous nucleic acid sequence is integrated into the MSCs' genomes.

5. The population of isolated mammalian MSCs of claim 1, wherein the heterologous nucleic acid sequence is a viral expression vector.

6. The population of isolated mammalian MSCs of claim 1, wherein the MSCs are rodent MSCs.

7. The population of isolated mammalian MSCs of claim 1, wherein the MSCs are human MSCs.

8. The population of isolated mammalian MSCs of claim 1, wherein the MSCs are bone marrow MSCs.

9. A method of modulating inflammatory M1 macrophages in a mammal, the method comprising:
administering the population of isolated mammalian MSCs of claim 1 to a mammal who has inflammation such that the population expresses the anti-inflammatory cytokine in an amount sufficient to modulate inflammatory M1 macrophages into an anti-inflammatory M2 macrophage phenotype in the mammal.

10. The method of claim 9, wherein the heterologous nucleic acid sequence is selected from the group consisting of a linear expression vector, a circular expression vector, a plasmid, and a viral expression vector.

11. The method of claim 9, wherein the heterologous nucleic acid sequence is integrated into the MSCs' genomes.

12. The method of claim 9, wherein the mammal has chronic inflammation, bone injury, osteoarthritis, rheumatoid arthritis, cardiovascular disease, hepatic inflammation, myocardial infarction, musculoskeletal inflammation, neurological inflammation, diabetes, or spinal cord injury.

13. The method of claim 9, wherein the isolated mammalian MSCs are human MSCs and the mammal is a human.

14. The method of claim 9, wherein the isolated mammalian MSCs are mouse MSCs and the mammal is a mouse.

15. The method of claim 9, wherein the isolated mammalian MSCs are rat MSCs and the mammal is a rat.

\* \* \* \* \*

SEQUENCE LISTING

<160> NUMBER OF SEQ ID NOS: 25

<210> SEQ ID NO 1
<211> LENGTH: 52
<212> TYPE: DNA
<213> ORGANISM: Artificial sequence
<220> FEATURE:
<223> OTHER INFORMATION: Synthetic sequence

<400> SEQUENCE: 1
gggaatttcc ggggactttc cgggaatttc cggggactttt ccgggaattt cc    52

<210> SEQ ID NO 2
<211> LENGTH: 70
<212> TYPE: DNA
<213> ORGANISM: Artificial sequence
<220> FEATURE:
<223> OTHER INFORMATION: Synthetic sequence

<400> SEQUENCE: 2
tggggacttt ccgctgggga ctttccgctg gggactttcc gctggggact ttccgctggg    60
gactttccgc                                                            70

<210> SEQ ID NO 3
<211> LENGTH: 10
<212> TYPE: DNA
<213> ORGANISM: Artificial sequence
<220> FEATURE:
<223> OTHER INFORMATION: Synthetic sequence

<400> SEQUENCE: 3
gggaatttcc                                                            10

<210> SEQ ID NO 4
<211> LENGTH: 10
<212> TYPE: DNA
<213> ORGANISM: Artificial sequence
<220> FEATURE:
<223> OTHER INFORMATION: Synthetic sequence

<400> SEQUENCE: 4
ggggactttc                                                            10

<210> SEQ ID NO 5
<211> LENGTH: 10
<212> TYPE: DNA
<213> ORGANISM: Artificial sequence
<220> FEATURE:
<223> OTHER INFORMATION: Synthetic sequence

<400> SEQUENCE: 5
gggactttcc                                                            10

<210> SEQ ID NO 6
<211> LENGTH: 11
<212> TYPE: DNA
<213> ORGANISM: Artificial sequence
<220> FEATURE:
<223> OTHER INFORMATION: Synthetic sequence

<400> SEQUENCE: 6
ggggactttc c                                                          11

<210> SEQ ID NO 7
<211> LENGTH: 14
<212> TYPE: DNA
<213> ORGANISM: Artificial sequence
<220> FEATURE:
<223> OTHER INFORMATION: Synthetic sequence

<400> SEQUENCE: 7
tggggacttt ccgc                                                       14

<210> SEQ ID NO 8
<211> LENGTH: 10
<212> TYPE: DNA

<210> SEQ ID NO 8
<211> LENGTH: 10
<212> TYPE: DNA
<213> ORGANISM: Artificial sequence
<220> FEATURE:
<223> OTHER INFORMATION: Synthetic sequence

<400> SEQUENCE: 8
aaaaaaaaaa     10

<210> SEQ ID NO 9
<211> LENGTH: 10
<212> TYPE: DNA
<213> ORGANISM: Artificial sequence
<220> FEATURE:
<223> OTHER INFORMATION: Synthetic sequence

<400> SEQUENCE: 9
aaaaaaaaaa     10

<210> SEQ ID NO 10
<211> LENGTH: 10
<212> TYPE: DNA
<213> ORGANISM: Artificial sequence
<220> FEATURE:
<223> OTHER INFORMATION: Synthetic sequence

<400> SEQUENCE: 10
aaaaaaaaaa     10

<210> SEQ ID NO 11
<211> LENGTH: 140
<212> TYPE: PRT
<213> ORGANISM: Mus musculus

<400> SEQUENCE: 11

Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
            20                  25                  30

Ile Ile Gly Ile Leu Asn Glu Val Thr Gly Glu Gly Thr Pro Cys Thr
        35                  40                  45

Glu Met Asp Val Pro Asn Val Leu Thr Ala Thr Lys Asn Thr Thr Glu
    50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                85                  90                  95

Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
    130                 135                 140

<210> SEQ ID NO 12
<211> LENGTH: 211
<212> TYPE: PRT
<213> ORGANISM: Mus musculus

<400> SEQUENCE: 12

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
           20                  25                  30

Gly Asp Phe Thr Glu Asp Thr Thr Pro Asn Arg Pro Val Tyr Thr Thr
             35                  40                  45

Ser Gln Val Gly Gly Leu Ile Thr His Val Leu Trp Glu Ile Val Glu
 50                  55                  60

Met Arg Lys Glu Leu Cys Asn Gly Asn Ser Asp Cys Met Asn Asn Asp
 65                  70                  75                  80

Asp Ala Leu Ala Glu Asn Asn Leu Lys Leu Pro Glu Ile Gln Arg Asn
                 85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
            115                 120                 125

Asn Asn Leu Lys Asp Asn Lys Lys Asp Lys Ala Arg Val Leu Gln Arg
130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
            180                 185                 190

Ile Leu Lys Ser Leu Glu Glu Phe Leu Lys Val Thr Leu Arg Ser Thr
            195                 200                 205

Arg Gln Thr
    210

<210> SEQ ID NO 13
<211> LENGTH: 178
<212> TYPE: PRT
<213> ORGANISM: Mus musculus

<400> SEQUENCE: 13

Met Pro Gly Ser Ala Leu Leu Cys Cys Leu Leu Leu Leu Thr Gly Met
 1               5                  10                  15

Arg Ile Ser Arg Gly Gln Tyr Ser Arg Glu Asp Asn Asn Cys Thr His
             20                  25                  30

Phe Pro Val Gly Gln Ser His Met Leu Leu Glu Leu Arg Thr Ala Phe
             35                  40                  45

Ser Gln Val Lys Thr Phe Phe Gln Thr Lys Asp Gln Leu Asp Asn Ile
 50                  55                  60

Leu Leu Thr Asp Ser Leu Met Gln Asp Phe Lys Gly Tyr Leu Gly Cys
 65                  70                  75                  80

Gln Ala Leu Ser Glu Met Ile Gln Phe Tyr Leu Val Glu Val Met Pro
                 85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
            115                 120                 125

Phe Leu Pro Cys Glu Asn Lys Ser Lys Ala Val Glu Gln Val Lys Ser
130                 135                 140

Asp Phe Asn Lys Leu Gln Asp Gln Gly Val Tyr Lys Ala Met Asn Glu
145                 150                 155                 160

```
Phe Asp Ile Phe Ile Asn Cys Ile Glu Ala Tyr Met Met Ile Lys Met
                165                 170                 175

Lys Ser

<210> SEQ ID NO 14
<211> LENGTH: 199
<212> TYPE: PRT
<213> ORGANISM: Mus musculus

<400> SEQUENCE: 14

Met Asn Cys Val Cys Arg Leu Val Leu Val Val Leu Ser Leu Trp Pro
1               5                   10                  15

Asp Arg Val Val Ala Pro Gly Pro Ala Gly Ser Pro Arg Val Ser
                20                  25                  30

Ser Asp Pro Arg Ala Asp Leu Asp Ser Ala Val Leu Leu Thr Arg Ser
            35                  40                  45

Leu Leu Ala Asp Thr Arg Gln Leu Ala Ala Gln Met Arg Asp Lys Phe
        50                  55                  60

Pro Ala Asp Gly Asp His Ser Leu Asp Ser Leu Pro Thr Leu Ala Met
65                  70                  75                  80

Ser Ala Gly Thr Leu Gly Ser Leu Gln Leu Pro Gly Val Leu Thr Arg
                85                  90                  95

Leu Arg Val Asp Leu Met Ser Tyr Leu Arg His Val Gln Trp Leu Arg
            100                 105                 110

Arg Ala Gly Gly Pro Ser Leu Lys Thr Leu Glu Pro Glu Leu Gly Ala
        115                 120                 125

Leu Gln Ala Arg Leu Glu Arg Leu Leu Arg Arg Leu Gln Leu Leu Met
    130                 135                 140

Ser Arg Leu Ala Leu Pro Gln Ala Ala Pro Asp Gln Pro Val Ile Pro
145                 150                 155                 160

Leu Gly Pro Pro Ala Ser Ala Trp Gly Ser Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
        195

<210> SEQ ID NO 15
<211> LENGTH: 131
<212> TYPE: PRT
<213> ORGANISM: Mus musculus

<400> SEQUENCE: 15

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
                20                  25                  30

Leu Lys Glu Leu Ile Glu Glu Leu Ser Asn Ile Thr Gln Asp Gln Thr
            35                  40                  45

Pro Leu Cys Asn Gly Ser Met Val Trp Ser Val Asp Leu Ala Ala Gly
        50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95
```

```
Ala Pro Thr Thr Val Ser Ser Leu Pro Asp Thr Lys Ile Glu Val Ala
                100                 105                 110

His Phe Ile Thr Lys Leu Leu Ser Tyr Thr Lys Gln Leu Phe Arg His
            115                 120                 125

Gly Pro Phe
        130

<210> SEQ ID NO 16
<211> LENGTH: 153
<212> TYPE: PRT
<213> ORGANISM: Homo sapiens

<400> SEQUENCE: 16

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 17
<211> LENGTH: 212
<212> TYPE: PRT
<213> ORGANISM: Homo sapiens

<400> SEQUENCE: 17

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125
```

```
Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
                195                 200                 205

Leu Arg Gln Met
    210
```

<210> SEQ ID NO 18
<211> LENGTH: 178
<212> TYPE: PRT
<213> ORGANISM: Homo sapiens

<400> SEQUENCE: 18

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 19
<211> LENGTH: 199
<212> TYPE: PRT
<213> ORGANISM: Homo sapiens

<400> SEQUENCE: 19

```
Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
                20                  25                  30

Pro Asp Pro Arg Ala Glu Leu Asp Ser Thr Val Leu Leu Thr Arg Ser
            35                  40                  45
```

```
Leu Leu Ala Asp Thr Arg Gln Leu Ala Ala Gln Leu Arg Asp Lys Phe
        50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Arg Leu Gln Leu Leu Met
        130                 135                 140

Ser Arg Leu Ala Leu Pro Gln Pro Pro Asp Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
                195

<210> SEQ ID NO 20
<211> LENGTH: 146
<212> TYPE: PRT
<213> ORGANISM: Homo sapiens

<400> SEQUENCE: 20

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
        50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
                100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Gln
        130                 135                 140

Phe Asn
145

<210> SEQ ID NO 21
<211> LENGTH: 31
<212> TYPE: DNA
<213> ORGANISM: Artificial sequence
<220> FEATURE:
<223> OTHER INFORMATION: Synthetic sequence
```

```
<400> SEQUENCE: 21
agagggtata taatggaagc tcgacttcca g                              31

<210> SEQ ID NO 22
<211> LENGTH: 115
<212> TYPE: DNA
<213> ORGANISM: Artificial sequence
<220> FEATURE:
<223> OTHER INFORMATION: Synthetic sequence

<400> SEQUENCE: 22
gggaatttcc gggGactttc cgggaatttc cggggactttt ccgggaatttt ccagatctgg    60 cctcggcggc caagcttaga cactagaggg tatataatgg aagctcgact tccag         115

<210> SEQ ID NO 23
<211> LENGTH: 31
<212> TYPE: DNA
<213> ORGANISM: Artificial sequence
<220> FEATURE:
<223> OTHER INFORMATION: Synthetic sequence

<400> SEQUENCE: 23
agagggtata taatggaagc tcgacttcca g                              31

<210> SEQ ID NO 24
<211> LENGTH: 22
<212> TYPE: DNA
<213> ORGANISM: Artificial Sequence
<220> FEATURE:
<223> OTHER INFORMATION: Synthetic sequence

<400> SEQUENCE: 24
tacgtcacta gttgagctcg ct                                        22

<210> SEQ ID NO 25
<211> LENGTH: 22
<212> TYPE: DNA
<213> ORGANISM: Artificial Sequence
<220> FEATURE:
<223> OTHER INFORMATION: Synthetic sequence

<400> SEQUENCE: 25
atgctaggta ccggtggctt ta                                        22
```